US006670182B1

(12) United States Patent
Pruss et al.

(10) Patent No.: US 6,670,182 B1
(45) Date of Patent: *Dec. 30, 2003

(54) ASSAYS FOR β-AMYLOID PROCESSING

(75) Inventors: Rebecca Pruss, Strasbourg (FR); John Huggins, Kent (GB); Guy Rautmann, Strasbourg (FR); Barbara Cordell, Palo Alto, CA (US); Jan Marian Scardina, San Carlos, CA (US); Ronald P. Mischak, Palo Alto, CA (US)

(73) Assignees: Aventis Pharmaceuticals Inc., Bridgewater, NJ (US); Scios Nova, Inc., Mountain View, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/027,258

(22) Filed: Feb. 20, 1998

Related U.S. Application Data
(60) Provisional application No. 60/067,389, filed on Feb. 24, 1997, provisional application No. 60/067,390, filed on Apr. 2, 1997, and provisional application No. 60/072,099, filed on Jul. 31, 1997.

(51) Int. Cl.$^7$ ................................. C12N 5/06

(52) U.S. Cl. ...................... 435/358; 435/353; 435/368; 435/369; 435/320.1; 536/23.5

(58) Field of Search ................................ 435/325, 353, 435/358, 368, 369, 320.1, 69.1; 536/23.5

(56) References Cited

U.S. PATENT DOCUMENTS

| | | |
|---|---|---|
| 5,220,013 A | 6/1993 | Ponte et al. |
| 5,221,607 A | 6/1993 | Cordell et al. |
| 5,231,000 A | 7/1993 | Majocha et al. |
| 5,455,169 A | 10/1995 | Mullan |

OTHER PUBLICATIONS

Ghattas et al., *Molecular and Cellular Biology*, vol. 11.12: pp. 5848–5859 (1991).
Harlow and Lane, *Antibodies: A Laboratory Manual*, Cold Spring Harbor Press (1988).
Fackrell, J., *Clin. Immunoassay*, vol. 8: pp. 213–219 (1985).
Yolken, R.H., *Rev. Infect. Dis.*, vol. 4: p. 35 (1982).
Yanisch–Peron et al., *Gene*, vol. 33: pp. 103–119 (1985).
Kozak, *Nature*, vol. 308: pp. 241–246. (1984).
Jang, et al., *J. Virology*, vol. 63: pp. 1651–1660 (1989).
Blasquez, et al., *Mol. Microbiol.*, vol. 5: pp. 1511–1518 (1991).
Higaki et al., *Neuron*, vol. 14: pp. 651–659 (1995).
Caporaso et al., *Proc. Natl. Acad. Sci. USA*, vol. 89: pp. 2252–2256 (1992).
Seubert et al., *Nature*, vol. 361: pp. 260–263 (1993).
Naidu et al., *Journal of Biological Chemistry*, vol. 270: pp. 1369–1374 (1995).
Busciglio et al., *Proc. Natl. Acad Sci.*, vol. 90: pp. 2092–2096 (1993).
Wong et al., *Proc. Natl. Acad. Sci.*, vol. 82: pp. 8729–8732 (1985).
Sambrook, et al., *Molecular Cloning*, vol. 3: pp. 16.30–16.31 (1989).
Sambrook et al., In *Molecular Cloning: A Laboratory Manual*, vol. 3: pp. 16.8–16.15, Cold Spring Harbor Press (1989).
Old and Primrose, In *Principles of Gene Manipulation*, pp. 307–310 (1994).
Boshart et al., *Cell*, vol. 41: pp. 521–530 (1985).
Wickens and Stephenson, *Science*, vol. 226: pp. 1045–1051 (1984).
Kozak, M. J., *Cell, Biol.*, vol. 108: pp. 229–241 (1989).
Weidmann et al, *Cell*, vol. 57: pp. 115–126 (1989).
Glenner and Wong, *Biochem. and Biophys. Res. Comm.*, vol. 120: pp. 885–890 (1984).
Schehr, *Nature Biotechnology*, vol. 15: pp. 19–20 (1997).
Selkoe, *Science*, vol. 275: pp. 630–631 (1997).
Lemaire et al., *Nucleic Acids Research*, vol. 172: pp. 517–522 (1989).
Ashall and Goate, *Trends in Biochemical Sciences*, vol. 19: pp. 42–46 (1994).
Hardy and Allsop, *Trends in Pharmological Sciences*, vol. 12: pp. 383–388 (1991).
Van Broeckhoven, et al., *Science*, vol. 248: pp. 1120–1123 (1990).
Levy, *Science*, vol. 24: pp. 1124–1126 (1990).
Goate et al., *Nature*, vol. 349: pp. 704–706 (1991).
Hardy et al., *Lancet*, vol. 337: pp. 1342–1343 (1991).
Harlin et al., *Nature*, vol. 353: pp. 844–846 (1991).
Murrell et al., *Science*, vol. 254: pp. 97–99 (1991).
Cordell, *Annual Review Of Pharmacology and Toxicology*, vol. 34: pp. 69–89 (1994).
Pierce et al., *The Journal of Neuroscience*, vol. 16: pp. 1083–1090 (1996).
Roberts, *The Lancet*, vol. 338: pp. 1422–1423 (1991).
Motte and Williams, *Acta Neuropathologica*, vol. 77: pp. 535–546 (1989).
Mann and Esiri, *Journal of the Neurological Sciences*, vol. 89: pp. 169–179 (1989).
Masters, *Proceedings of the National Academy of Sciences*, vol. 82: pp. 4245–4249 (1985).
Ponte et al., *Nature*, vol. 311: pp. 525–527 (1988).

(List continued on next page.)

*Primary Examiner*—James Ketter
(74) *Attorney, Agent, or Firm*—Michael J. Schmeizer

(57) ABSTRACT

The invention relates to the design, construction and use of eukaryotic cell lines useful in the identification of inhibitors of β-amyloid processing. More specifically, the invention relates to in vitro assays capable of identifying or quantifying a 4.2 kDa β-amyloid protein. The present invention also provides for DNA and protein molecules for the design, construction and use of eukaryotic cell lines useful in the identification of inhibitors of β-amyloid processing.

26 Claims, 6 Drawing Sheets

OTHER PUBLICATIONS

Schehr, *Bio/Technology*, vol. 12: pp. 140–144 (1994).
Neve et al., *Neuron* vol. 1: pp. 669–677 (1988).
Haass et al., *Nature*, vol. 359: pp. 322–325 (1992).
Tanzi et al., *Nature*, vol. 331: pp. 528–530 (1988).
Shoji et al., *Science*, vol. 258: pp. 126–129 (1992).
Wolf et al., *The EMBO Journal*, vol. 9.7: pp. 2079–2084 (1990).

↑ STRONG RIBOSOME BINDING SITE ENCODING SEQUENCE

↑ STRONG RIBOSOME BINDING SITE ENCODING SEQUENCE

DAEFRHDSGYEVH<u>HQKLVFFAED</u>VGSNKGAIIGLMVGG<u>VV</u>IAT
             Y                                    Y Y
        mAb 1101.1                      BA#1 mAb 108.1

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 67 amino acids
      (B) TYPE: amino acid
      (C) STRANDEDNESS: single
      (D) TOPOLOGY: linear (ii) MOLECULE TYPE: None (xi) SEQUENCE DESCRIPTION: SEQ ID NO:1:

```
Asp Arg Gly Leu Thr Thr Arg Pro Gly Ser Gly Leu Thr Asn Ile Lys
1               5                   10                  15

Thr Glu Glu Ile Ser Glu Val Lys Met Asp Ala Glu Phe Arg His Asp
            20                  25                  30

Ser Gly Tyr Glu Val His His Gln Lys Leu Val Phe Phe Ala Glu Asp
        35                  40                  45

Val Gly Ser Asn Lys Gly Ala Ile Ile Gly Leu Met Val Gly Gly Val
    50                  55                  60

Val Ile Ala
65
```

(2) INFORMATION FOR SEQ ID NO:2:

(i) SEQUENCE CHARACTERISTICS:
      (A) LENGTH: 43 amino acids
      (B) TYPE: amino acid
      (C) STRANDEDNESS: single
      (D) TOPOLOGY: linear (ii) MOLECULE TYPE: None (xi) SEQUENCE DESCRIPTION: SEQ ID NO:2:

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
            35                  40
```

(2) INFORMATION FOR SEQ ID NO:3:

(i) SEQUENCE CHARACTERISTICS:
      (A) LENGTH: 14 base pairs

```
       (B) TYPE: nucleic acid
       (C) STRANDEDNESS: single
       (D) TOPOLOGY: linear (xi) SEQUENCE DESCRIPTION: SEQ ID NO:3:

GCCGCCAGCC AUGG                                                      14

(2) INFORMATION FOR SEQ ID NO:4:

(i) SEQUENCE CHARACTERISTICS:
       (A) LENGTH: 9 base pairs
       (B) TYPE: nucleic acid
       (C) STRANDEDNESS: single
       (D) TOPOLOGY: linear (xi) SEQUENCE DESCRIPTION: SEQ ID NO:4:

CCCCGATGC                                                             9

(2) INFORMATION FOR SEQ ID NO:5:

(i) SEQUENCE CHARACTERISTICS:
       (A) LENGTH: 35 base pairs
       (B) TYPE: nucleic acid
       (C) STRANDEDNESS: single
       (D) TOPOLOGY: linear (xi) SEQUENCE DESCRIPTION: SEQ ID NO:5:

TTTTCAAAGC TTACCATGCT GCCCGGTTTG CACTG                                35

(2) INFORMATION FOR SEQ ID NO:6:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (xi) SEQUENCE DESCRIPTION: SEQ ID NO:6:

AGGCTGCTCT AGAGGGGGTC TAGTTCTGCA T                                    31

(2) INFORMATION FOR SEQ ID NO:7:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (xi) SEQUENCE DESCRIPTION: SEQ ID NO:7:

GGTGGAAGAA GAAGAAGCC                                                  19

(2) INFORMATION FOR SEQ ID NO:8:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:8:

GTGACGAGGC CGAGGAGGAA C                                               21
```

ASSAYS FOR β-AMYLOID PROCESSING

CROSS REFERENCE TO RELATED APPLICATIONS

This application claims the benefit under 35 U.S.C. §119(e) of U.S. Provisional Application Ser. No. 60/067,389, filed Feb. 24, 1997, which was converted from application Ser. No. 08/804,971 on Sep. 30, 1997. This application also claims the benefit under 35 U.S.C. §119(e) of U.S. Provisional Application Ser. No. 60/067/390, filed Apr. 2, 1997, which was converted from application Ser. No. 08/825,737 on Sep. 30, 1997, which is a continuation-in-part of U.S. Pat. application Ser. No. 08/804,971, filed Feb. 24, 1997. This application also claims the benefit under 35 U.S.C. §119(e) of U.S. Provisional Application Ser. No. 60/072,099 filed Jul. 31, 1997, which was converted from application Ser. No. 08/904,296 on Dec. 19, 1997, which is a continuation-in-part of U.S. Pat. application Ser. No. 08/825,737, filed Apr. 2, 1997, which is a continuation-in-part of U.S. Pat. application Ser. No. 08/804,971, filed Feb. 24, 1997.

FIELD OF THE INVENTION

The invention relates to the design, construction and use of eukaryotic cell lines useful in the identification of inhibitors of β-amyloid processing. More specifically, the invention relates to in vitro assays capable of identifying or quantifying 4.2 kDa β-amyloid protein. The present invention also provides for DNA and protein molecules for the design, construction and use of eukaryotic cell lines and in vitro assays useful in the identification of inhibitors of β-amyloid processing.

BACKGROUND OF THE INVENTION

Alzheimer's disease has emerged as a significant health problem. It is estimated that over 5% of the U.S. population and over 15% of the U.S. population over 85 are beset with some form of Alzheimer's disease (Cross, *Eur. J. Pharmacol.* 82: 77–80 (1982); Terry, et al.,*Ann. Netirol.* 14:497–506 (1983)). Currently, there is no remission in the progression of the disease, nor is there any truly effective pharmaceutical intervention or method for diagnosing the disease (Schehr, Bio/Technology 12: 140–144 (1994); Cordell, *Ann. Rev. Pharmacol. Toxicol.* 34: 69–89 (1994), herein incorporated by reference). A patient with Alzheimers progresses toward increasing mental and physical incapacitation.

A characteristic feature of Alzheimer's disease is the formation or deposit of β-amyloid plaques in affected individuals. Mature β-amyloid plaques are often associated with degenerating neuronal processes. β-amyloid deposits are not solely associated with persons suffering from Alzheimer's disease but are also associated with persons suffering from other amyloidoses, for example, brain trauma or Downs syndrome (Cordell, *Ann. Rev. Pharmacol. Toxicol.* 34: 69–89 (1994); Pierce et al., *Journal of Neuroscience,* 16: 1083–1090 (1996); Roberts,*Lancet* 338:1422–1423 (1991); Motte and Williams,*Acta Neuropathol* 77: 535–546 (1989); Mann and Esiri, *Journal of the Neurological Sciences* 89: 169–179 (1989); Masters, *Proc. Natl. Acad. Sci.,* 82: 4245–4249 (1985)).

The β-amyloid proteins isolated from neuritic plaques are self aggregating moieties termed the 4.2 kDa β-amyloid protein or alternatively termed one of the following: the A4 protein (Ponte et al., *Nature* 311: 525–527 (1988), herein incorporated by reference); the β-amyloid peptide (Schehr, Bio/Technology 12: 140–144 (1994), herein incorporated by reference); 4.2 kDa β-amyloid polypeptide (Neve et al., *Neuron* 1: 669–677 (1988), herein incorporated by reference); 4K peptide or AP (Haas et al., *Nature* 359: 322–325 (1992), herein incorporated by reference); amyloid B-protein or amyloid A4 (Tanzi et al., *Nature* 331: 528–530 (1988), herein incorporated by reference); 4 kD amyloid 5 protein, βAP or 4 kD protein (Shoji et al., *Science* 258: 126–129 (1992), herein incorporated by reference); the 4.2–4.5 kd amyloid protein subunit (Wolf et al., *EMBO* 9.7: 2079–2084 (1990), herein incorporated by reference); β protein (Weidmann et al., *Cell* 57:115–126 (1989); the beta-amyloid core protein (Cordell, U.S. Pat. No. 5,221,607, herein incorporated by reference); a composition of peptides individually referred to as Aβ1-39 peptide, Aβ1-40 peptide, Aβ1-41 peptide and Aβ1-42 peptide (described in Glenner and Wong, *Biochem. Biophys. Res. Comm.* 120: 885–890 (1984), herein incorporated by reference; (Schehr, *Nature Biotechnology* 15: 19–20 (1997), herein incorporated by reference) and Aβ1-43 peptide (Shoji et al., *Science* 258: 126–129 (1992); Selkoe, *Science* 275: 630–631 (1997), herein incorporated by reference). Aβ1-39 peptide, Aβ1-40 peptide, Aβ1-41 peptide, Aβ1-42 peptide and Aβ1-43 peptide comprise 39, 40, 41, 42 and 43 amino acids respectively.

Characterization of cDNA encoding the 4.2 kDa β-amyloid protein showed that the 4.2 kDa β-amyloid protein was transcribed as part of a larger precursor protein, β-amyloid precursor protein (APP)(Lemaire et al., *Nucleic Acid Research* 17: 517–22 (1989)). Three major APP protein isoforms, $APP_{695}$, $APP_{751}$ and $APP_{770}$, have been characterized (Cordell, *Ann. Rev. Pharmacol. Toxicol.* 34: 69–89 (1994)). The isoforms $APP_{695}$, $APP_{751}$ and $APP_{770}$, contain respectively, 695, 751 and 770 amino acids (Weidmann et al., *Cell* 57:115–126 (1989), herein incorporated by reference). These isoforms are the result of differential splicing of the primary APP RNA transcript. The $APP_{695}$ isoform differs from the longer isoforms in not containing the Kunitz proteinase inhibitor domain (Lemaire, et al., *Nucleic Acids Research* 172: 517–522 (1989); herein incorporated by reference); Mullan, U.S. Pat. No. 5,455,169, herein incorporated by reference); Ponte et al., *Nature* 331: 525–527 (1988), herein incorporated by reference). The mRNA corresponding to the $APP_{695}$ isoform also differs from the longer isoforms in that it has been shown to be preferentially expressed in the brain (Neve et al., *Neuron* 1: 669–677 (1988)).

Certain APP mutations have been reported (Ashall and Goate, *Trends in Biochemical Sciences,* 19: 42–46 (1994), herein incorporated by reference); Hardy and Allsop, *Trends in Pharmological Sciences* 12: 383–388 (1991), herein incorporated by reference). Examples of characterized APP mutants include: the "Swedish FAD double mutant" (Mullan et al., *Nature Genetics* 1: 345–347 (1992), herein incorporated by reference), the "London mutant" (Van Broeckhoven, et al., *Science* 248: 1120–1123 (1990), herein incorporated by reference); Levy, *Science* 24: 1124–1126 (1990), herein incorporated by reference; valine$^{717}$→isoleucine mutant (Goate et al., *Nature* 349: 704–706 (1991), herein incorporated by reference); Hardy et al., *Lancet* 337: 1342–1343 (1991), herein incorporated by reference); valine$^{717}$→glycine mutant (Harlan et al., *Nature* 353: 844–846 (1991); and valine$^{717}$→phenylalanine mutant (Murrell et al., *Science* 254: 97–99 (1991), herein incorporated by reference).

In each of the APP isoforms, the 4.2 kDa β-amyloid protein corresponds to an internal region that begins 99 residues from the carboxyl terminal end of the APP isoforms (Shoji et al., *Science* 258: 126–129 (1992)). Two major pathways of APP processing have been reported (See Higaki et al., *Neuron* 14: 651–659 (1995), herein incorporated by reference). One pathway involves proteolytic cleavages that result in the formation of truncated carboxyl terminal 8–12 kD remnants (Caporaso et al., *Proc. Natl. Acad. Sci. USA* 89: 2252–2256 (1992), herein incorporated by reference). It has been reported that carboxyl terminal 8–12 kD remnants are nonamyloidgenic (Seubert et al., *Nature* 361:260–263 (1993), herein incorporated by reference). It is suggested that the proteolytic processing of APP in this pathway occurs at a number of intracellular and membrane locations (See Higaki et al., *Neuron* 14: 651–659 (1995)). The carboxyl terminal 8–12 kD remnants have been reported to remain cell-associated, possibly due to retention of a transmembrane domain within the carboxyl terminal 8–12 kD remnants (Cordell, *Ann. Rev. Pharmacol. Toxicol.* 34: 69–89 (1994)). The second processing pathway has been reported to be associated with the endosomal/lysosomal system and it is this pathway that is reportedly responsible for the production of the 4.2 kDa β-amyloid protein (See Higaki et al., *Neuron* 14: 651–659 (1995)).

Cell lines capable of producing a 4.2 kDa β-amyloid protein have been reported (Naidu et al., *Journal of Biological Chemistry* 270: 1369–1374 (1995), herein incorporated by reference; Higaki et al., *Neuron* 14: 651–669 (1995), herein incorporated by reference). Naidu et al. and Higaki et al. report the establishment of the CP-6 cell line by stably transfecting a human cDNA encoding the 695-amino acid isoform of β-amyloid precursor protein, driven by a β-actin promoter, into Chinese hamster ovary fibroblasts. Busciglio et al. report transient transfection of a COS cell line (a monkey cell line containing part of the SV 40 early promoter) with an expression plasmid under the control of a cytomegalovirus promoter, which overexpressed the 695-amino acid isoform of β-amyloid precursor protein (Busciglio et al., *Proc. Natl. Acad Sci.* 90: 2092–2096 (1993), herein incorporated by reference). In addition, Haass et al. report stable transfection of kidney cell lines which overexpressed the 695-amino acid isoform of β-amyloid precursor protein (Haass et al., *Nature* 359: 322–325 (1992)).

Cordell, et al., U.S. Pat. No. 5,221,607, reports stably expressing two different proteins in chinese hamster cells. These proteins are 99 and 42 amino acids respectively corresponding to an amyloid protein of 99 amino acids and the beta-amyloid core protein. In both cases, protein expression was facilitated by the use of a β-actin promoter. Again, in both cases, the selectable marker the bacterial neomycin gene) was genetically linked to a second, different promoter (SV40 early promoter).

Cell lines transfected with a human cDNA encoding the 695-amino acid isoform of β-amyloid precursor protein have been used to screen putative inhibitors of the β-amyloid processing pathway (Higaki et al., *Neuron* 14: 651–669 (1995)). Higaki et al. report a inhibition assay carried out in 10 cm dishes (Higaki et al., *Neuron* 14: 651–669 (1995)). The CP-6 cells utilized by Higaki et al. in their inhibitor assay were propagated in 10 cm dishes containing a 1:1 mixture of growth media supplemented with 200 μl inhibitor, 200 μl leupeptin, 200 μl E64, 100 μl chloroquine and 30 mM $NH_4Cl$, 30 mM $NH_4$-acetate, 30 mM methylamine, 10 μM monesin and 10 μM brefeldin A (Higaki et al., *Neuron* 14: 651–669 (1995)).

In another inhibition assay, described in Patent Application PCT/US93/01014, herein incorporated by reference, a human embryonic cell line, which had been stably transfected with a vector containing the cDNA encoding for the $APP_{751}$ isoform. This transfected cell line was utilized to screen potential inhibitors of a 22 kDa pre-amyloid intermediate.

Antibodies or antiserum specific to epitopes located within a 4.2 kDa β-amyloid protein have been reported (Ponte and Cordell, U.S. Pat. No. 5,220,013, herein incorporated by reference; Majocha et al., U.S. Pat. No. 5,231,000; amyloid beta antibodies cat. nos. 0490-1916, 0490-1858, 0490-1857, ANAWA Biomedical Services & Products, Wangen Switzerland; mouse monoclonal anti-β-amyloid peptide (1-28), Zymed Laboratories, South San Francisco, Calif.; mouse anti-beta amyloid monoclonal cat no. RDI-BAMYLOID, Research Diagnostics, Inc. Flanders, N.J.). For example, Naidu et al. report antiserum reactive to epitopes located within the carboxyl terminus of a 4.2 kDa β-amyloid protein and Busciglio et al. report serum containing antibodies raised against a short peptide region of a 4.2 kDa β-myloid protein (amino acids 28–40) (Naidu et al., *Journal of Biological Chemistry* 270: 1369–1374 (1995); and Busciglio et al., *Proc. Natl. Acad Sci.* 90: 2092–2096 1993)). In addition, monoclonal antibodies reactive to epitopes located within a 4.2 kDa β-amyloid protein have been reported (Haass et al., *Nature* 359: 322–325 (1992)). Haass et al. report a monoclonal antibody, 6C6, which is reactive against an epitope contained within a short peptide region of a 4.2 kDa β-amyloid protein (amino acids 1–16) and a monoclonal antibody, 266, which is reactive against a different epitope contained within a short peptide region of a 4.2 kDa β-amyloid protein (Haass et al., *Nature* 359: 322–325 (1992)). In addition, Patent Application PCT/US93/01014 describes a number of antibodies directed against a variety of regions found within the $APP_{751}$ isoform.

A significant problem associated with cell lines, such as CP-6 (Naidu et al., *Journal of Biological Chemistry* 270: 1369–1374 (1995); and Higaki et al., *Neuron* 14: 651–669 (1995)), is that the level of the 4.2 kDa β-amyloid protein produced by such cell lines is lower than is necessary for automated measurement. Due to the insufficient level of expression in cell lines, such as CP-6, the volume of cells necessary for accurate and routine measurement is not suitable for routine high throughput screening.

The present invention provides cell lines that express an APP protein at a level sufficient for high throughput screening. High throughput screening of inhibitors is typically carried out using 96 well microtitre dishes, which can contain cells in a volume of about 250 μl. The volume and surface area constraints associated with 96 well microtitre plates, place a premium on cell lines capable of expressing the desired protein at high levels.

SUMMARY OF THE INVENTION

The invention relates to the design, construction and use of eukaryotic cell lines useful in the identification of inhibitors of β-amyloid processing. More specifically, the invention relates to in vitro assays capable of identifying or quantifying a 4.2 kDa β-amyloid protein. The present invention also provides for DNA and protein molecules for the design, construction and use of eukaryotic cell lines and in vitro assays useful in the identification of inhibitors of β-amyloid processing.

An object of the present invention is an eukaryotic cell line having a exogenous gene construction, the exogenous gene construction comprising a cytomegalovirus promoter encoding sequence, a strong ribosome binding site encoding sequence, β-amyloid precursor protein encoding sequence, a selectable marker encoding sequence, and a poly-adenylation signal encoding sequence.

Another object of the present invention is an eukaryotic cell line selected from the group consisting of 21-N-1, 21-N-2, 21-N-3, 21-N-4, 21-N-5, 21-N-6, 21-N-7, 21-N-8, and 21-N-9 or a derivative thereof.

Another object of the present invention is an eukaryotic cell line capable of producing greater than 30 ng 4.2 kDa β-amyloid protein molecule per mg protein.

Another object of the present invention is an eukaryotic cell line that produces a 4.2 kDa β-amyloid protein molecule to a greater extent than a CP-7 cell line.

Another object of the present invention is an eukaryotic cell line that produces a 4.2 kDa β-amyloid protein molecule to a greater extent than a CP-6 cell line Another object of the present invention is an eukaryotic cell line that produces a Aβ1-40 peptide molecule to a greater extent than a CP-7 cell line.

Another object of the present invention is an eukaryotic cell line that produces a Aβ1-42 peptide molecule to a greater extent than a CP-7 cell line.

Another object of the present invention is an eukaryotic cell line having a exogenous gene construction, the exogenous gene construction comprising a cytomegalovirus promoter encoding sequence, a ribosome binding site encoding sequence, a β-amyloid precursor protein encoding sequence, a selectable marker encoding sequence, and a poly-adenylation signal encoding sequence.

Another object of the present invention is a substantially purified nucleic acid molecule that encodes, in order: a cytomegalovirus promoter; a ribosome binding site; a β-amyloid precursor protein molecule; a selectable marker; and a poly-adenylation signal. A further object of the present invention is a substantially purified nucleic acid molecule that encodes, in order: a cytomegalovirus promoter; a strong ribosome binding site; a β-amyloid precursor protein molecule; a selectable marker; and a poly-adenylation signal.

Another object of the present invention is a method for identifying an inhibitor of β-amyloid processing pathway comprising: administering the inhibitor to a eukaryotic cell line having an exogenous gene construction, the exogenous gene construction comprising a cytomegalovirus promoter encoding sequence, a strong ribosome binding site encoding sequence, a amyloid precursor protein encoding sequence, a selectable marker encoding sequence, and a poly-adenylation signal encoding sequence; and quantifying a protein molecule that is indicative of inhibition of β-amyloid processing pathway.

Another object of the present invention is a method for identifying an inhibitor of β-amyloid processing pathway comprising, (a) incubating an inhibitor of β-amyloid processing and a eukaryotic cell line to produce a protein molecule that is indicative of inhibition of β-amyloid processing pathway in a medium containing a labeled amino acid, the eukaryotic cell line having a exogenous gene construction, the exogenous gene construction comprising a cytomegalovirus promoter encoding sequence, a strong ribosome binding site encoding sequence, a β-amyloid precursor protein encoding sequence, a selectable marker encoding sequence, and a poly-adenylation signal encoding sequence, where the exogenous gene construction is capable of stably expressing a β-amyloid precursor protein molecule; (b) separating the eukaryotic cell line and the medium; (c) separating the protein molecule from the eukaryotic cell line and the medium; and (d) quantifying the protein molecule.

A further object of the present invention is a high through-put assay for identification of an inhibitor of β-amyloid processing comprising: (a) incubating an inhibitor of β-amyloid processing and a eukaryotic cell line to produce a protein molecule that is indicative of inhibition of β-amyloid processing pathway, the eukaryotic cell line having a exogenous gene construction, the exogenous gene construction comprising a cytomegalovirus promoter encoding sequence, a strong ribosome binding site encoding sequence, a β-amyloid precursor protein encoding sequence, a selectable marker encoding sequence, and a poly-adenylation signal encoding sequence (b) quantifying the protein molecule produced by the incubation step.

DETAILED DESCRIPTION OF THE INVENTION

I. Overview of the Invention

Figure 1:
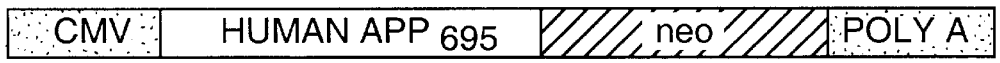
FIG. 1 shows a diagrammatic representation of a region of selected plasmids between the immediate early gene transcription enhancer/promoter from cytomegalovirus and a polyadenylation signal from SV40 virus.
Figure 1:
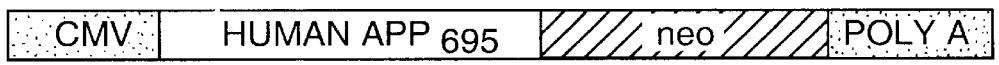
Figure 1:
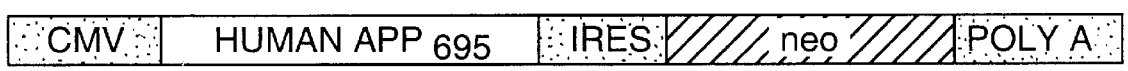
Figure 1:

The invention relates to the design, construction and use of eukaryotic cell lines useful in the identification of inhibitors of β-amyloid processing. More specifically, the invention relates to in vitro assays capable of identifying or quantifying a 4.2 kDa β-amyloid protein. The present invention also provides for DNA and protein molecules for the design, construction and use of eukaryotic cell lines and in vitro assays useful in the identification of inhibitors of β-amyloid processing.

II. Agents and Definitions

As used herein, an agent be it naturally occurring molecule or otherwise may be "substantially purified," if desired, such that one or more molecules that is or may be present in a naturally occurring preparation containing that molecule will have been removed or will be present at a lower concentration than that at which it would normally be found.

The agents of the present invention will preferably be "biologically active" with respect to either a structural attribute, such as the capacity of a nucleic acid to hybridize to another nucleic acid molecule, or the ability of a protein to be bound by antibody (or to compete with another molecule for such binding). Alternatively, such an attribute may be catalytic, and thus involve the capacity of the agent to mediate a chemical reaction or response.

The agents of the present invention comprise cell lines, nucleic acid molecules, proteins, and organic molecules.

As used herein, the term "4.2 kDa β-amyloid protein" refers, without limitation, to all of following: the A4 protein; the β-amyloid peptide; 4.2 kDa β-amyloid polypeptide; 4K peptide or Aβ; amyloid B-protein; amyloid A4; 4 kD amyloid β protein; βAP; 4 kD protein; the 4.2–4.5 kd amyloid protein subunit; β protein; and the beta-amyloid core protein. In addition, as used herein, the term refers to an approximately 4 kDa protein or peptide identified by Wong et al., *Proc. Nat. Acad. Sci.* 82: 8729–8732 (1985), herein incorporated by reference; Master et al., *Proc. Nat.* 4245–4249 (1985), herein incorporated by reference, which is defined by amino acid sequence analysis as a mixture of four peptides with slightly different amino termini, the amino termini of the three smaller peptides being internal to the largest peptide.

As used herein the terms "Aβ1-39 peptide", "Aβ1-40 peptide", "Aβ1-41 peptide", "Aβ1-42 peptide" and "Aβ1-43 peptide" refer to certain peptide constituents of the 4.2 kDa β-amyloid protein. The Aβ1-39 peptide consists of 39 amino acids, the Aβ1-40 peptide consists of 40 amino acids, Aβ1-41 peptide consists of 41 amino acids, Aβ1-42 peptide consists of 42 amino acids and Aβ1-43 peptide consists of 43 amino acids. These peptides can be heterogenous at their N termini.

As used herein, the term "protein molecule" or "peptide molecule" includes any molecule that comprises five or more amino acids. It is well know in the art that proteins may undergo modification, including post-translational modifications, such as, but not limited to, disulfide bond formation, glycosylation, phosphorylation, or oligomerization. Thus, as used herein, the term "protein molecule" or "peptide molecule" includes any protein molecule that is modified by any biological or non-biological process. The terms "amino acid" and "amino acids" refer to all naturally occurring L-amino acids. This definition is meant to include norleucine, ornithine, and homocysteine.

As used herein, the term "exogenous gene construction" is any DNA, whether naturally occurring or otherwise, from any source, that is capable of being inserted into any organism.

As used herein, "transfection" or "transformation" refers to any process for altering the DNA content of a eukaryotic cell. This includes, without limitation, calcium phosphate or DEAE-dextran-mediated transfection, polybrene transfection, protoplast fusion transfection, electroporation transfection, liposome transfection, and direct microinjection transfection or such other means for effecting controlled DNA uptake as are known in the art (See Sambrook, et al., *Molecular Cloning* 3: 16.30–16.31 (1989), herein incorporated by reference).

As used herein, "stably expressing" refers to any eukaryotic cell or any eukaryotic cell line capable of producing a desired protein molecule over a desired time frame.

As used herein, "efficient expression of β-amyloid precursor protein" refers to the expression level of β-amyloid precursor protein that is greater than cell lines CP-6 or CP-7.

As used herein, "stably transformed" or "stably transfected" with reference to any eukaryotic cell or any eukaryotic cell line refers to any eukaryotic cell or any eukaryotic cell line having an exogenous gene construction, which is capable of generating progeny comprising the same exogenous gene construction.

As used herein, the terms "β-amyloid precursor protein" or "APP protein" refers to isoforms $APP_{695}$, $APP_{751}$ and $APP_{770}$ or mutant thereof. Mutants of APP include, without limitation,: the Swedish FAD double mutant; the "London mutant; the valine$^{717}$→isoleucine mutant; valine$^{717}$→glycine mutant; and the valine$^{717}$→phenylalanine mutant.

As used herein, a "β-amyloid precursor protein or derivative thereof" is any β-amyloid precursor protein or protein or peptide fragment that corresponds to any protein or peptide fragment that is greater than five amino acids that is identical to any contiguous amino acid sequence located within the β-amyloid precursor protein.

As used herein the terms "β-amyloid precursor encoding sequence mRNA" or "APP mRNA" refers to any messenger RNA that is capable of specifically hybridizing, in whole or in part to any part of any β-amyloid precursor encoding sequence.

As used herein the terms "β-amyloid precursor encoding sequence" or "APP encoding sequence" refer to any DNA molecule that encodes a $APP_{695}$, $APP_{751}$ and $APP_{770}$ or mutant thereof. Mutants of APP include, without limitation, the Swedish FAD double mutant; the "London mutant; the valine$^{71}$→isoleucine mutant; valine$^{717}$→glycine mutant; and the valine$^{717}$→phenylalanine mutant.

As used herein, the term "internal ribosome entry site encoding sequence" or "IRES encoding sequence" is any nucleic acid sequence that can help facilitate the translation of more than one protein encoding sequence from a single promoter.

As used herein, the term "encoding sequence" refers to a sequence having a specified characteristic. This "encoding sequence" can, without limitation, be non-transcribed, transcribed, non-translated or translated.

As used herein, the term "inhibitor" refer to any molecule that effects the processing of β-amyloid precursor protein.

As used herein, the term "β-amyloid precursor pathway" is any biological process or a step within a biological process that modifies β-amyloid precursor protein.

As used herein, the term "media" or "medium" is any composition capable of sustaining the desired cells.

As used herein a "strong ribosome binding site encoding sequence" or a "strong Kozak encoding sequence" is any ribosome binding site encoding sequence or Kozak encoding sequence that has a purine at position −3 (relative the ATG initiation codon) and a guanine at position +4 (relative to the ATG initiation codon).

As used herein, a "weak ribosome binding site encoding sequence" or a "weak Kozak encoding sequence" is any ribosome binding site encoding sequence or Kozak encoding sequence that lacks a purine at position-3 (relative the ATG initiation codon) or lacks a guanine at position +4 (relative to the ATG initiation codon).

As used herein, a "high throughput assay" is any assay capable of being carried out in its entirety in a reaction volume less than about 500 µl.

As used herein, two nucleic acid molecules are said to be capable of specifically hybridizing to one another if the two molecules are capable of forming an anti-parallel or reverse complementary, double-stranded nucleic acid structure.

(A) Cell Lines

An embodiment of the present invention is an eukaryotic cell line having an exogenous gene construction, the exogenous gene construction comprising a cytomegalovirus promoter encoding sequence, a strong ribosome binding site encoding sequence, a β-amyloid precursor protein encoding sequence, a selectable marker encoding sequence, and a poly-adenylation signal encoding sequence.

Another embodiment of the present invention is an eukaryotic cell line having a exogenous gene construction, the exogenous gene construction comprising a cytomegalovirus promoter encoding sequence, a ribosome binding site encoding sequence, a β-amyloid precursor protein encoding sequence, a selectable marker encoding sequence, and a poly-adenylation signal encoding sequence.

The eukaryotic cell line of the present invention may be any cell line having a exogenous gene construction capable of expressing a β-amyloid precursor protein. In a preferred embodiment of the present invention, the eukaryotic cell line is selected from the group consisting of chinese hamster ovary cell line, chinese hamster ovary cell line K1, dihydrofolate reductase deficient hamster cell line, human kidney cell line, rat neuroglimo cell line, human neuroglimo cell line, and rat neuroblastoma cell line. In a more preferred embodiment of the present invention, the eukaryotic cell line is a chinese hamster ovary cell line. In an even more preferred embodiment of the present invention, the eukaryotic cell line is the chinese hamster ovary cell line K1.

The eukaryotic cell line having an exogenous gene construction of the present invention may be any cell line transformed or transfected with an exogenous gene construction. In a preferred embodiment of the present invention, the eukaryotic cell line having an exogenous gene construction of the present invention may be any cell line stably transformed or stably transfected with an exogenous gene construction.

In an embodiment, exogenous gene construction is any DNA, whether naturally occurring or otherwise, from any source, that is capable of being inserted into any organism. Preferably, exogenous gene construction is any DNA, whether naturally occurring or otherwise, from any source that is capable of being stably introduced into eukaryotic cells.

The β-amyloid precursor protein encoding sequence may encode any APP protein or derivative. In a preferred embodiment, the β-amyloid precursor protein may encode an APP protein selected from the group consisting of three major APP protein isoforms, $APP_{695}$, $APP_{751}$ and $APP_{770}$, and the "Swedish FAD double mutant", the "London mutant", the valine$^{717}$→isoleucine mutant, the valine$^{717}$→glycine mutant, the valine$^{717}$→phenylalanine mutant. In an even more preferred embodiment the β-amyloid precursor protein encoding sequence may encode the $APP_{695}$ protein isoform.

The selectable marker encoding sequence may be any sequence that encodes a protein which facilitates the identification of cells that have an exogenous gene construction. In a preferred embodiment, the selectable marker encoding sequence is selected from the group consisting of: neomycin phosphotransferase encoding sequence; dihydrofolate reductase encoding sequence; xanthine-guanine phosphoribosyltransferase encoding sequence; aspartate transcarbamoylase encoding sequence; adenosine deaminase encoding sequence; adenylate deaminase encoding sequence; UMP synthetase encoding sequence; glutamine synthetase encoding sequence; asparagine synthetase encoding sequence; ornithine decarboxylase encoding sequence; the thymidine kinase encoding sequence; the aminoglycosidase phosphotransferase encoding sequence; hygromycin B phosphotransferase encoding sequence; and the CAD encoding sequence (see, for example, Sambrook et al., In *Molecular Cloning: A Laboratory Manual*, 16.8–16.15, Cold Spring Harbor Press (1989), herein incorporated by reference; Old and Primrose, In *Principles of Gene Manipulation*, 307–310 (1994), herein incorporated by reference). In an even more preferred embodiment the selectable marker is encoded by the neomycin phosphotransferase gene.

The promoter encoding sequence of the present invention is any promoter including requisite transcription enhancer sequences capable of stably expressing high levels of β-amyloid precursor encoding sequence mRNA or 4.2 kDa β-amyloid protein in a transfected eukaryotic cell line. In a preferred embodiment, the promoter encoding sequence is the immediate early gene human cytomegalovirus promoter and associated transcription enhancer elements (Boshart et al., *Cell* 41: 521–530 (1985), herein incorporated by reference). In an even more preferred embodiment of the present invention, the promoter encoding sequence corresponding to −601 to −14 as set forth in FIG. 3 of Boshart et al., *Cell* 41: 521–530 (1985).

During the expression of eukaryotic genes, RNA polymerase II transcribes through the site where a termination signal is present. The sequence elements of the polyadenylation site is recognized and polyadenylation will then occur. Consequently, the 3' terminus of the mature mRNA is formed by site specific cleavage and polyadenylation. Two distinct elements are often required for accurate and efficient polyadenylation: (1) GU or U-rich sequences located downstream from the polyadenylation site and (2) a highly conserved sequence of six nucleotides as described by Wickens and Stephenson, *Science* 226:1045–1051(1984), herein incorporated by reference and Sambrook et al., 16:6, In *Molecullar Cloning: A Laboratory Manual*, Cold Spring Harbor Press (1989), herein incorporated by reference.

The poly-adenylation signal encoding sequence of the present invention is any encoding sequence that is required for accurate and efficient polyadenylation. In a preferred embodiment of the polyadenylation signal encoding sequence is derived from SV40. In an even more preferred embodiment, the poly-adenylation signal encoding sequence of the present invention is as described by Wickens and Stephenson, *Science* 226:1045–1051 (1984). In a further preferred embodiment, the polyadenylation signal comprises a transcription termination signal.

The β-amyloid precursor protein of the present invention is any β-amyloid precursor protein or derivative thereof. In a preferred embodiment of the present invention the β-amyloid precursor protein or derivative thereof is selected from the group consisting of isoforms $APP_{695}$, $APP_{751}$ and $APP_{770}$ or a mutant thereof. Potential mutants of β-amyloid precursor protein include, without limitation, the Swedish FAD double mutant; the London mutant; the valine$^{717}$→isoleucine mutant; valine$^{717}$→glycine mutant; and the valine$^{717}$→phenylalanine mutant. In an even more preferred embodiment of the β-amyloid precursor protein of the present invention is $APP_{695}$.

An embodiment of the present invention is to provide eukaryotic cell lines which produce a 4.2 kDa β-amyloid protein to a greater extent than eukaryotic cell line CP-6 or CP-7.

An embodiment of the present invention is to provide eukaryotic cell lines which produce a 4.2 kDa β-amyloid protein to a greater extent than eukaryotic cell line CP-7. In a preferred embodiment, the eukaryotic cell lines of the present invention produce greater than two fold more 4.2 kDa β-amyloid protein than eukaryotic cell line CP-7. In a more preferred embodiment, the eukaryotic cell lines of the present invention produce greater than four fold more 4.2 kDa β-amyloid protein than eukaryotic cell line CP-7. In an even more preferred embodiment, the eukaryotic cell lines of the present invention produce greater than six fold more 4.2 kDa β-amyloid protein than eukaryotic cell line CP-7.

In particularly preferred embodiments, the eukaryotic cell lines of the present invention produce (i) greater than eight fold more 4.2 kDa β-amyloid protein than eukaryotic cell line CP-7 or (ii) produce greater than ten fold more 4.2 kDa β-amyloid protein than eukaryotic cell line CP-7 or (iii) be suitable for use in a high throughput assay.

An embodiment of the present invention is to provide eukaryotic cell lines which produce a Aβ1-40 peptide to a greater extent than eukaryotic cell line CP-7. In a preferred embodiment, the eukaryotic cell lines of the present invention produce greater than two fold more Aβ1-40 peptide than eukaryotic cell line CP-7. In a more preferred embodiment, the eukaryotic cell lines of the present invention produce greater than three fold more Aβ1-40 peptide than eukaryotic cell line CP-7. In an even more preferred embodiment, the eukaryotic cell lines of the present invention produce greater than 3.5 fold more Aβ1-40 peptide than eukaryotic cell line CP-7.

An embodiment of the present invention is to provide eukaryotic cell lines which produce a Aβ1-42 peptide to a greater extent than eukaryotic cell line CP-7. In a preferred embodiment, the eukaryotic cell lines of the present invention produce greater than two fold more Aβ1-42 peptide than eukaryotic cell line CP-7. In a more preferred embodiment, the eukaryotic cell lines of the present invention produce greater than three fold more Aβ1-42 peptide than eukaryotic cell line CP-7. In an even more preferred embodiment, the eukaryotic cell lines of the present invention produce greater than four fold more Aβ1-42 peptide than eukaryotic cell line CP-7. In particularly preferred embodiment, the eukaryotic cell lines of the present invention produce greater than six fold more Aβ1-42 peptide than eukaryotic cell line CP-7.

An embodiment of the present invention is to provide a eukaryotic cell line that produces greater than about 30 ng 4.2 kDa β-amyloid protein/mg protein as measured or quantified by RIA. In a more preferred embodiment of the present invention, the eukaryotic cell line of present invention produces greater than about 40 ng 4.2 kDa β-amyloid protein/mg protein as measured or quantified by RIA. In an even more preferred embodiment of the present invention, the eukaryotic cell line of present invention produces greater than about 50 ng 4.2 kDa β-amyloid protein/mg protein as measured or quantified by RIA. In a particularly preferred embodiment of the present invention, the eukaryotic cell line of the present invention produces greater than about 60 ng 4.2 kDa β-amyloid protein/mg protein as measured or quantified by RIA. In an even more preferred embodiment of the present invention, the eukaryotic cell line of the present invention produces greater than about 65 ng 4.2 kDa β-amyloid protein/mg protein as measured or quantified by RIA. In a particularly preferred embodiment of the present invention, the eukaryotic cell line of the present invention produces greater than about 70 ng 4.2 kDa β-amyloid protein/mg protein as measured or quantified by RIA.

An embodiment of the present invention is to provide eukaryotic cell lines which produce a higher relative amount of APP mRNA, as detected by RT-PCR, than the cell line designated CP-7.

In a preferred embodiment, the secretion rate for the eukaryotic cell lines of the present invention is estimated at about 4 ng of 4.2 kDa β-amyloid protein (total) per 100 μl medium during 4 hours when cells are cultured at density of 0.5×1×10$^5$ cells per well in 96 well plates (surface area ~0.4 cm$^2$). In a preferred embodiment, the secretion rate for the eukaryotic cell lines of the present invention is estimated at about 5 ng of 4.2 kDa β-amyloid protein (total) per 100 μl medium during 4 hours when cells are cultured at density of 0.5×1×10$^5$ cells per well in 96 well plates (surface area ~0.4 cm$^2$).

The consensus sequence for initiation of translation by eukaryotic ribosomes is GCC GCC A$^{-3}$/GCC A$^1$UGG$^4$ (SEQ ID NO: 3), Kozak, M. *J. Cell. Biol.* 108: 229–241 (1989), herein incorporated by reference; Sambrook et al., 16.16, In *Molecular Cloning: A Laboratory Manual,* Cold Spring Harbor Press (1989), herein incorporated by reference. It has reported that, for practical purposes, an initiation of translation by eukaryotic ribosomes is considered "strong" or "weak" by considering positions labeled −3 and +4. As long as there is a purine (A or G) at position −3 and a guanine at +4. An illustration of a weak ribosome binding site encoding sequence or a weak Kozak encoding sequence can be found between the β-actin promoter and an APP$_{695}$ encoding sequence present in CP-6 cells as utilized by Higaki et al., ((5'-CCC CGA TGC-3' (SEQ ID NO: 4)(Higaki et al., *Neuron* 14: 651–669 (1995)).

The ribosome binding site encoding sequence of the present invention is any sequence that initiates translation by eukaryotic ribosomes. In a preferred embodiment of the present invention, the ribosome encoding sequence of the present invention is a strong ribosome binding site encoding sequence. In an even more preferred embodiment the ribosome binding site encoding sequence of the present invention is found within the following sequence: 5'-TTT TCA AAG CTT ACC ATG CTG CCC GGT TTG CAC TG-3' ( NO: 5).

The IRES encoding sequence of the present invention is any sequence that facilitates the translation of a β-amyloid precursor protein or derivative thereof encoding sequence and a selectable marker encoding sequence from a single messenger RNA transcript and single promoter. In a preferred embodiment of the present invention, the IRES encoding sequence facilitates the translation of the 695 isoform of human β-amytoid precursor protein and the encoding sequence for bacterial neomycin transferase. In a even more preferred embodiment of the IRES encoding sequence of the present invention is an encephalomycarditis virus IRES (Ghattas et al., *Molecular and Cellular Biology* 11.12: 5848–5859 (1991), herein incorporated by reference).

In a particularly preferred embodiment of the present invention, a single cytomegalovirus promoter encoding sequence is capable of co-expressing a β-amyloid precursor protein encoding sequence and a selectable marker encoding sequence.

(B) Nucleic Acid Molecules

An object of the present invention is a substantially purified nucleic acid molecule that encodes, in order: a cytomegalovirus promoter; a ribosome binding site; a β-amyloid precursor protein; a selectable marker; and a poly-adenylation signal.

Another object of the present invention is a substantially purified nucleic acid molecule that encodes, in order: a cytomegalovirus promoter; a strong ribosome binding site; a β-amyloid precursor protein; a selectable marker; and a poly-adenylation signal.

Another object of the present invention is a substantially purified nucleic acid molecule that encodes, in order: a cytomegalovirus promoter; a ribosome binding site; a β-amyloid precursor protein; internal ribosome entry site; a selectable marker; and a poly-adenylation signal.

Another object of the present invention is a substantially purified nucleic acid molecule that encodes, in order: a cytomegalovirus promoter; a strong ribosome binding site; a β-amyloid precursor protein; internal ribosome entry site; a selectable marker; and a poly-adenylation signal.

It is also understood that any of the exogenous gene constructions of the present invention described above are nucleic acid molecules of the present invention. It is further understood that any of the nucleic acid molecules of the present invention can be substantially purified and/or be biologically active.

Practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., In *Molecular Cloning: A Laboratory Manual,* Cold Spring Harbor Press (1989), herein incorporated by reference.

(C) Antibodies

One aspect of the present invention concerns antibodies, single-chain antigen binding molecules, or other proteins that specifically bind to any β-amyloid precursor protein or derivative thereof and their analogs, fusions or fragments. As used herein, an antibody or peptide is said to "specifically bind" to any β-amyloid precursor protein or derivative thereof and their analogs, fusions or fragments if such binding is not competitively inhibited by the presence of non-β-amyloid precursor protein or derivative thereof and its analogs, fusions or fragments.

Practitioners are familiar with the standard resource materials which describe specific conditions and procedures for the construction, manipulation and isolation of antibodies (see, for example, Harlow and Lane, *In Antibodies: A Laboratory Manual* Cold Spring Harbor Press (1988), herein incorporated by reference). Antibodies which specifically bind to any β-amyloid precursor protein or derivative thereof and its analogs, fusions or fragments may be prepared using such techniques.

Preferred examples of antibodies or antisera that specifically bind β-amyloid precursor protein or derivative thereof and its analogs, fusions or fragments comprise the following: monoclonal antibodies 1101.1 (1101.1 was deposited with the American Tissue Type Collection, Rockville, Md. on Apr. 25, 1997 and assigned ATCC No HB12347), 1702.1 (1702.1 was deposited with the American Tissue Type Collection, Rockville, Md. on Jun. 3, 1997 and assigned ATCC No HB12363) and 108.1 (108.1 was deposited with the American Tissue Type Collection, Rockville, Md. on Jun. 3, 1997 and assigned ATCC No HB12362) and antisera BA#1 , BA#2, amyloid beta antibodies cat. nos. 0490-1916, 0490-1858, 0490-1857 (ANAWA Biomedical Services & Products, Wangen Switzerland); mouse monoclonal anti-β-amyloid peptide (1-28) (Zymed Laboratories, South San Francisco, Calif.); mouse anti-beta amyloid monoclonal cat no. RDI-BAMYLOID, Research Diagnostics, Inc. Flanders, N.J. Particularly preferred examples of antibodies or antisera that specifically bind β-amyloid precursor protein or derivative thereof and its analogs, fusions or fragments are selected from the following: monoclonal antibodies 1101.1, 1702.1 and 108.1 and antisera BA#1 and BA#2.

(D) Indicative Protein Molecules

One aspect of the present invention concerns indicative protein molecules. In an embodiment of the present invention, the protein molecule that is indicative of inhibition of β-amyloid processing pathway is any protein molecule. In a preferred embodiment of the present invention, the protein molecule that is indicative of inhibition of β-amyloid processing pathway is any β-amyloid precursor protein or derivative thereof. In a more preferred embodiment of the present invention the protein molecule that is indicative of inhibition of β-amyloid processing pathway is selected from the group consisting of 4.2 kDa β-amyloid protein, Aβ1-39 peptide, Aβ1-40 peptide, Aβ1-41 peptide, Aβ1-42 peptide, Aβ1-43 peptide, truncated carboxyl terminal 8–12 kD remnants, 99 amino acid protein as described by Cordell, et al., U.S. Pat. No. 5,221,607, a 22 kDa pre-amyloid intermediate as described in PCT/US93/01014, and the 3 kDa peptides including the reported product of α- and γ-secretase and 3B, which includes peptides 12-39, 12-40, 12-42 and 12-43 as described herein.

In an even more preferred embodiment of the present invention the protein molecule that is indicative of inhibition of β-amyloid processing pathway is selected from the group consisting of 4.2 kDa β-amyloid protein, Aβ1-39 peptide, Aβ1-40 peptide, Aβ1-41 peptide, Aβ1-42 peptide, and Aβ1-43 peptide. In another even more preferred embodiment of the present invention the protein molecule that is indicative of inhibition of β-amyloid processing pathway is selected from the group consisting of 4.2 kDa β-amyloid protein, Aβ1-40 peptide, and Aβ1-42 peptide. In another even more preferred embodiment of the present invention the protein molecule that is indicative of inhibition of β-amyloid processing pathway is the 4.2 kDa β-amyloid protein. Variation in the composition or pattern of APP products can be indicative of inhibitors of (α-, β, γ-secretase.

III. Uses of the Agents of the Invention

An embodiment of the present invention is a method for identifying an inhibitor of β-amyloid processing pathway comprising: administering the inhibitor to a eukaryotic cell line having a exogenous gene construction, the exogenous gene construction comprising a cytomegalovirus promoter encoding sequence, a strong ribosome binding site encoding sequence, β-amyloid precursor protein encoding sequence, a selectable marker encoding sequence, and a poly-adenylation signal encoding sequence; and quantifying a protein molecule that is indicative of inhibition of β-amyloid processing pathway.

Another embodiment of the present invention is a method for identifying an inhibitor of β-amyloid processing pathway comprising, (a) incubating an inhibitor of β-amyloid processing and a eukaryotic cell line to produce a protein molecule that is indicative of inhibition of β-amyloid processing pathway in a medium containing a labeled amino acid, the eukaryotic cell line having a exogenous gene construction, the exogenous gene construction comprising a cytomegalovirus promoter encoding sequence, a strong ribosome binding site encoding sequence, a β-amyloid precursor protein encoding sequence, a selectable marker encoding sequence, and a poly-adenylation signal encoding sequence, where the exogenous gene construction is capable of stably expressing a β-amyloid precursor protein molecule; (b) separating the eukaryotic cell line and the medium; (c) separating protein molecule from the eukaryotic cell line and the medium; and (d) quantifying the protein molecule.

A further embodiment of the present invention is a high throughput assay for identification of an inhibitor of β-amyloid processing comprising: (a) incubating an inhibitor of β-amyloid processing and a eukaryotic cell line to produce a protein molecule that is indicative of inhibition of β-amyloid processing pathway, the eukaryotic cell line having a exogenous gene construction, the exogenous gene construction comprising a cytomegalovirus promoter encoding sequence, a strong ribosome binding site encoding sequence, a β-amyloid precursor protein encoding sequence, a selectable marker encoding sequence, and a polyadenylation signal encoding sequence; and (b) quantifying the protein molecule produced by the incubation step.

In another particularly preferred embodiment, the high throughput assay of the present invention may be carried out or undertaken in a volume of less than about 300 µl. In another more particularly preferred embodiment, the high throughput assay of the present invention may be carried out or undertaken in a volume of less than about 250 µl. In another even more particularly preferred embodiment, the high throughput assay of the present invention may be carried out or undertaken in a volume of about 200 µl. It is understood that the volume of the high throughput assay of the present invention may vary during the high throughput assay. As used herein, the terms "be carried out" in a specified volume or "undertaken" in a specified volume means that the entire high throughput assay, including all reagents, cell line or other biological materials or chemicals utilized never at, any temporal stage, during the assay exceed the specified volume. However, it is understood that the total volume of reagents, cell lines or other biological materials or chemicals utilized by the high throughput assay of the present invention may exceed the specified volume In another particularly preferred embodiment, the high throughput assay of the present invention may be carried out on a surface area of less than about 1 $cm^{-2}$. In another more particularly preferred embodiment, the high throughput assay of the present invention may be carried out on a surface area less than about 0.6 $cm^{-2}$. In another even more particularly preferred embodiment, the high throughput assay of the present invention may be carried out on a surface area of less than about 0.4 $cm^{-2}$. As used herein, the "surface area" refers to the area in physical contact with a eukaryotic cell line.

Incubation of the eukaryotic cells in the absence of an inhibitor of the present invention may be for any period of time and under any appropriate conditions for cell growth or maintenance. Incubation of the eukaryotic cells with an inhibitor of β-amyloid processing of the present invention may be for any period of time and under any appropriate conditions for cell growth or maintenance.

In a preferred embodiment of the high throughput assay of the present invention, the incubation of an inhibitor of β-amyloid processing and a eukaryotic cell line to produce a protein molecule that is indicative of inhibition of β-amyloid processing pathway may be carried out for between about 1 hour and about 20 hours. In an even more preferred embodiment of the high throughput assay of the present invention, the incubation of an inhibitor of β-amyloid processing and a eukaryotic cell line to produce a protein molecule that is indicative of inhibition of β-amyloid processing pathway may be carried out for between about 2 hours and about 10 hours. In a particularly preferred embodiment of the high throughput assay of the present invention, the incubation of an inhibitor of β-amyloid processing and a eukaryotic cell line to produce a protein molecule that is indicative of inhibition of β-amyloid processing pathway may be carried out for between about 3 hours and about 5 hours.

Any conventional 96-well polystyrene microtiter dishes used in diagnostic laboratories and in tissue culture may be used with this invention. Methods for synthesizing polystyrene are known in the art; such methods are disclosed in, for example, treatises on plastics and polymers such as Byrdson, J. A. , *Plastics Materials,* Fifth Edition, Butterworth Heinemann, London (1991), herein incorporated by reference; Maxisorb plate (Nunc, Rochester, N.Y.).

The level of a protein molecule indicative of inhibition of β-amyloid processing pathway may be measured or quantified using any of the techniques known in the art. For example, any of a wide array of immunoassays formats may be used for this purpose (Harlow and Lane, *Antibodies: A Laboratory Manual,* Cold Spring Harbor Press (1988), herein incorporated by reference; Fackrell, *J. Clin. Innunoassay* 8:213–219 (1985), herein incorporated by reference; Yolken, R. H., *Rev. Infect. Dis.* 4:35 (1982), herein incorporated by reference; Collins, W. P., In *Alternative Immunoassays,* John Wiley & Sons, N.Y. (1985), herein incorporated by reference; Ngo, T. T. et al., In *Enzyme Mediated Immunoassay,* Plenum Press, N.Y. (1985), herein incorporated by reference).

The simplest immunoassay involves merely incubating an antibody that is capable of binding to a predetermined target molecule with a sample suspected to contain the target molecule. The presence of the target molecule is determined by the presence, and proportional to the concentration, of any antibody bound to the target molecule. In order to facilitate the separation of target-bound antibody from the unbound antibody initially present, a solid phase is typically employed. Thus, for example, the sample can be passively bound to a solid support, and, after incubation with the antibody, the support can be washed to remove any unbound antibody.

In more sophisticated immunoassays, the concentration of the target molecule is determined by binding the antibody to a support, and then permitting the support to be in contact with a sample suspected of containing the target molecule. Target molecules that have become bound to the immobilized antibody can be detected in any of a variety of ways. For example, the support can be incubated in the presence of a labeled, second antibody that is capable of binding to a second epitope of the target molecule. Immobilization of the labeled antibody on the support thus requires the presence of the target, and is proportional to the concentration of the target in the sample. In an alternative assay, the target is incubated with the sample and with a known amount of labeled target. The presence of target molecule in the sample competes with the labeled target molecules for antibody binding sites. Thus, the amount of labeled target molecules that are able to bind the antibody is inversely proportional to the concentration of target molecule in the sample.

In general, immunoassay formats employ either radioactive labels ("RIAs") or enzyme labels ("ELISAs"). RIAs have the advantages of simplicity, sensitivity, and ease of use. Radioactive labels are of relatively small atomic dimension, and do not normally affect reaction kinetics. Such assays suffer, however, from the disadvantages that, due to radioisotopic decay, the reagents have a short shelf-life, require special handling and disposal, and entail the use of complex and expensive analytical equipment. RIAs are described in *Laboratory Techniques and Biochemistry in Molecular Biology,* by Work, T. S., et al., North Holland Publishing Company, N.Y. (1978), with particular reference to the chapter entitled "An Introduction to Radioimmune Assay and Related Techniques" by Chard, T., incorporated by reference herein. ELISAs have the advantage that they can be conducted using inexpensive equipment, and with a myriad of different enzymes, such that a large number of detection strategies—calorimetric, pH, gas evolution, etc.— can be used to quantitate the assay. In addition, the enzyme reagents have relatively long shelf-lives, and lack the risk of radiation contamination that attends to RIA use. ELISAs are described in *ELISA and Other Solid Phase Immunoassays* (Kemeny, D. M. et al., Eds.), John Wiley & Sons, N.Y. (1988), incorporated by reference herein.

It is further understood that the level (i.e., the concentration of a protein molecule that is indicative of inhibition of β-amyloid processing pathway, etc.) or pattern (i.e., the kinetics of expression, rate of decomposition, stability profile of a protein molecule that is indicative of inhibition of β-amyloid processing pathway, etc.) may be measured or quantified.

The following examples are presented to illustrate the present invention and to assist one of ordinary skill in making and using the same. The examples are not intended in any way to otherwise limit the scope of the invention.

EXAMPLE 1

Cloning of Human $APP_{695}$

The DNA region encoding the human $APP_{695}$ isoform is amplified using 5' and 3' primers. The sequence of the 5' primer is as follows: 5'-TTT TCA <u>AAG CTT</u> ACC <u>*ATG*</u> CTG CCC GGT TTG CAC TG-3' (SEQ ID NO: 5). The 5' primer contains a HindIII, restriction endonuclease site (underlined) and, for efficient ribosome binding, a purine (adenosine) at the −3 position (italics) relative to the initiation ATG (underlined/italics). The sequence of the 3' primer is as follows: 5'-A GGC <u>TGC TCT AGA</u> GGG GGT CTA GTT CTG CA <u>*T*</u>-3'(SEQ ID NO: 6). Within the 3' primer is an XbaI restriction endonuclease site (underlined) separated by five nucleotides from a stop codon. The stop sequence corresponds to stop sequence located within the cDNA (underlined/italics). A polymerase chain reaction (PCR) reaction is carried out using the 5' and 3' primer in combination with the plasmid β-actin-β-actin$_{695}$ (Scios Nova, Mountain View, Calif.) as the template. The PCR product is digested with HindIII and XbaI and ligated to pBluescript-SK (Stratagene, La Jolla, Calif.), which is precut with HindIII and XbaI. The insert is confirmed by sequencing.

EXAMPLE 2

Construction of an Expression Vector Capable of Expressing High Levels of $APP_{695}$ Using standard molecular cloning methods, a DNA vector to transform cells is constructed, which contains a bacterial origin of replication and β-lactamase gene derived from pUC19 (Yanisch-Peron et al., *Gene* 33:103–119 (1985), herein incorporated by reference), the immediate early gene transcription enhancer/promoter from cytomegalovirus (Boshart, M, et al., *Cell* 41:521–530 (1985), herein incorporated by reference), the coding sequence for human $APP_{695}$ modified to include a Kozak consensus sequence at the 5' end for efficient ribosome binding (Kozak, *Nature* 308:241–246. (1984), herein incorporated by reference), an internal ribosome entry site (IRES) from encephalolmyocarditis virus (Jang, et al., *J. Virology* 63:1651–1660 (1989), herein incorporated by reference) the *E. coli* gene for aminoglycoside phosphotransferase (neo)( Blazquez, et al., *Mol. Microbiol.* 5:1511–1518 (1991), herein incorporated by reference); and a polyadenylation signal from SV40 virus (Wickens and Stephenson, *Science* 226:1045–1051 (1984), herein incorporated by reference). A diagrammatic representation of the region of the plasmid between the immediate early gene transcription enhancer/promoter from cytomegalovirus and a polyadenylation signal from SV40 virus is set out in FIG. 1.

Figure 2:
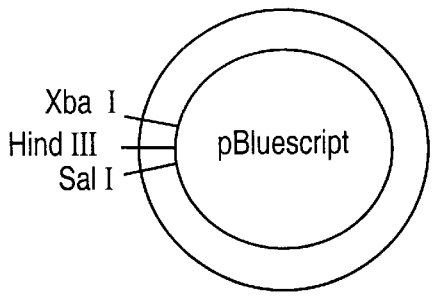
FIG. 2 shows a diagrammatic representation of a construction strategy of pCMV-IRES-βAPP$_{695}$.
Figure 2:
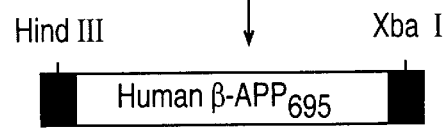
Figure 2:
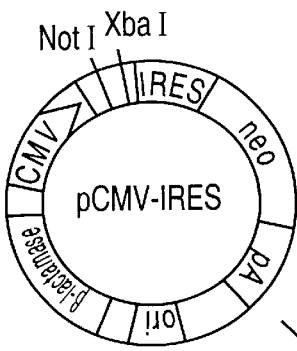
Figure 2:
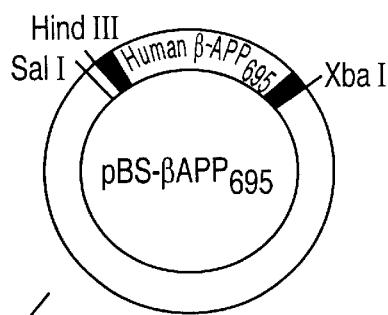
Figure 2:
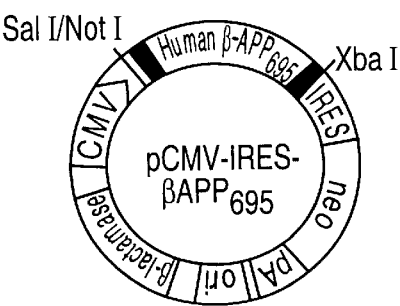

The cloning steps are essentially as follows: The human $APP_{695}$ insert is removed from pBluescript-SK by digesting with SalI followed by a fill-in reaction to produce blunt ends. The resulting DNA is then digested with XbaI. The insert is isolated by agarose gel electrophoresis followed by purification of the DNA from the excised gel band. The plasmid pCMV-IRES is digested with NotI. The digested DNA is then filled-in to produce blunt ends. The filled-in DNA is then digested with XbaI. The human $APP_{695}$ insert (described above) is ligated to the digested plasmid to produce pCMV-IRES-β$APP_{695}$. The construction strategy is diagramatically illustrated in FIG. 2.

EXAMPLE 3

Stable Transfection of Chinese Hamster Ovary Cells

Chinese hamster ovarY cells are transfected by liposome-mediated DNA transfection with either 16 or 32 μg of pCMV-IRES-β$APP_{695}$ and selected for stable integration of the human $APP_{695}$ and neo transcription unit as follows. CHO-K1 cells (American Type Culture Collection, 12301 Parklawn Drive, Rockville, Md. 20852, USA) are routinely cultured in the following medium: DMEM/NUT MIX F-12 (Gibco 041-01331M, Gaithersburg, Md.); 1% Non-essential amino acids; 2.5 mM L-glutamine; 0.5 mM Pyruvate; 1% Penicillin, 1% Streptomycin; 10% Fetal calf serum (Gibco 011-06290 (Australia)). Cells are subcultured onto 150 cm² plates four days prior to transfection to obtain an expected density of 70% confluence by the day of transfection. DNA is mixed with lipofectamine reagent (GIBCO/BRL, Gaithersburg, Md.). The cells are then transfected according to the manufacture's directions (GIBCO/BRL, Gaithersburg, Md.), herein incorporated by reference, overnight and refed with fresh medium the following day. Three days after transfection, cells are placed in medium containing 1 mg/ml geneticin and allowed to grow for three to four weeks. Colonies arising from surviving cells are collected by mild trypsinization, transferred to individual wells of a 96 well dish and cultured in medium without geneticin. Cells are expanded and evaluated for the expression of APPm-RNA.

EXAMPLE 4

Analysis of APP mRNA Expression

RNA is extracted from cells rising from individual isolates using RNA Now (Biogenex, San Ramon, Calif.) and analyzed for the presence of human APP transcripts by reverse transcriptase-polymerase chain reaction (RT-PCR). The reverse transcriptase reaction is primed with random hexamers and the PCR amplification is performed using primers designed to amplify a-600 bp fragment of human APP mRNA (5' primer: 5'-GGTGGAAGAAG-AAGAAGCC-3' (SEQ ID NO:7); 3' primer: 5'-GTGACGAGGCCGAGGAGGAAC-3' (SEQ ID NO:8). The colonies are scored for the presence and relative amount of APP compared to CP-6 cells (See Table 1). CP-6 is a CHO cell line expressing human $APP_{695}$ under control of the β-actin promoter (Higaki et al., *Neuron* 14:651–669 (1995)).

TABLE 1

| Clone | DNA μg | PCR | RIA ηM |
|---|---|---|---|
| 21-N-A | 16 | 1+ | 0.51 |
| 21-N-B | 16 | 1+ | 0.66 |
| 21-N-C | 16 | 3+ | 2.64 |
| 21-N-D | 16 | 3+ | 0.47 |
| 21-N-E | 16 | 3+ | 0.21 |
| 21-N-F | 16 | 0 | ND |
| 21-N-G | 16 | 0 | ND |
| 21-N-H | 16 | 0 | ND |
| 21-N-I | 16 | 3+ | 0.46 |
| 21-N-I | 16 | 3+ | 0.66 |
| 21-N-K | 16 | 1+ | 0.71 |
| 21-N-L | 16 | 1+ | 1.01 |
| 21-N-M | 16 | 1+ | 1.01 |
| 21-N-N | 16 | 2+ | 0.37 |
| 21-N-O | 16 | 3+ | 5.40 |
| 21-N-P | 16 | 1+ | 0.84 |
| 22-N-A | 32 | 1+ | 1.13 |
| 22-N-B | 32 | 0 | ND |
| 22-N-C | 32 | 1+ | 0.88 |
| 22-N-D | 32 | 1+ | 0.71 |
| 22-N-E | 32 | 1+ | 0.92 |
| 22-N-F | 32 | 2+ | 0.37 |
| 22-N-G | 32 | 1+ | 0.80 |
| 22-N-H | 32 | 2+ | 0.37 |
| CP-6 | — | 2+ | ND |
| CP-7 | — | — | 0.85 |

In Table 1, PCR results are expressed as the relative amount of APP mRNA detected by RT-PCR and ND refers to values not determined.

EXAMPLE 5

Radioimmunoassay analysis of the 4.2 kDa β-amyloid protein

Cell lines are assayed for the production of 4.2 kDa β-amyloid protein by radioimmunoassay (RIA) following reverse phase chromatography to concentrate 4.2 kDa β-amyloid protein from assay medium. Rabbit BA#1 antiserum and iodinated Aβ1-40 peptide are used in the RIA. The cells are incubated for 5 hours in RIA assay medium (EMEM (Gibco 041-01090M, Gaithersburg, Md.), 1% non-essential amino acids, 2 mM L-glutamine, 1% Penicillin, 1% Streptomycin) containing 1% FCS and Aβ peptide concentrate. After incubation, RIA assay medium is removed from cells, centrifuged at 1,500 rpm for 10 minutes then stored frozen at −20° C. 1.5–2 ml of medium is passed through a using Lichrolut cartridges (Merck, N.J.) or Sepak C18 cartridges (Waters Corp., Mass.), which are then washed first with 2 ml 5% $CH_3CN$ in 0.1% TFA and then washed with 2 ml 25% $CH_3CN$ in 0.1% TFA. The 4.2 kDa β-amyloid protein is eluted with 2 ml 50% $CH_3CN$ in 0.1% TFA, dried by speedvac centrifugation and then stored frozen at −20° C. Concentrated peptides are re-dissolved in 250 μl of 0.1% Triton-X 100+0.1% BSA in water.

The RIA is carried out as follows: Aβ1-40 peptide is labeled with $^{125}I$ using the chloramine T method (Amersham, Arlington Heights, Ill.), and purified by reverse phase HPLC on a C18 column (Vydac, Hesperia, Calif.) using a linear gradient from 20% to 50% $CH_3CN$ in 0.1% TFA. The labeled peptide is eluted at 40% $CH_3CN$, and stored at −20° C.

To glass 12×75 mm tubes are added in order; 100 μl BA#1 antiserum diluted 1:150 in Buffer A (0.1 M sodium phosphate, pH 7.4+0.1% BSA+0.1% Triton-X 100) or 1% bovine serum albumin in PBS, 2× the concentration necessary to bind 30% of the labeled peptide in the absence of competing ligand, 50 μl unknown samples, peptide standards (Aβ1-40 peptide, Bachem, King of Prussia, Pa.) diluted in Buffer A or 1% bovine serum albumin in PBS to concentrations ranging from 0.4–100 nM (resulting in final concentrations of 0.1–25 nM—standards are prepared from a 1 mg/ml stock solution dissolved in 20% isopropanol and stored at −20° C.)), total binding (Buffer A or 1% bovine serum albumin in PBS is used for total binding) or non-specific binding (10 μM Aβ1-40 peptide in Buffer A or 1% bovine serum albumin in PBS is used to measure total displacement/nonspecific binding) and 50 μl HPLC purified $^{125}I$-A-1-40 peptide diluted in Buffer C to give between 8,000–10,000 cpm/tube. The solution is made up to a total volume 200 μl.

The solution is then vortexed and incubated overnight at 4° C. After incubation, 50 μl normal rabbit serum is added to the sample followed by 800 μl 15.8% polyethylene glycol (MW 6,000–8,000) dissolved in Buffer A or 1% bovine serum albumin in PBS. The sample is then incubated for 10 minutes at 4° C. Following incubation, the sample is centrifuged for 20 minutes at 3,200 rpm (Sorvall T600B). After pelleting the sample, the supernatant is aspirated and radioactivity of the pellets is measured in a gamma counter.

Figures 3, 5:
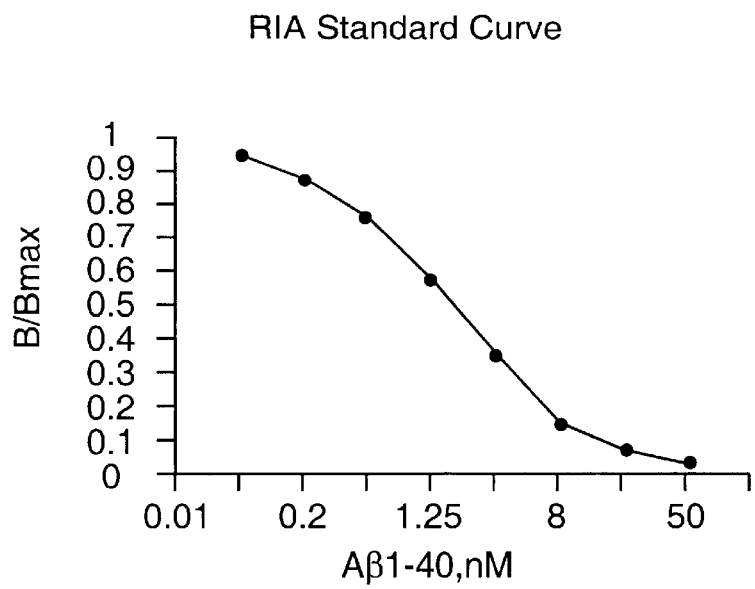
FIG. 3 shows a typical standard curve using RIA.
FIG. 5 diagrammatically represents the epitopes recognized by antibodies BA#1, 108.1, 1702.1 and 1101.1 (SEQ ID NO: 2).

A typical standard curve using the RIA is shown in FIG. 3. Results obtained from cells generated from these two transfections are summarized in Table 1 and is the average of two media samples, each assayed in duplicate. The five most positive clones are further evaluated for the effect of different media on 4.2 kDa β-amyloid protein secretion and stability. These results are summarized in Table 2. Certain cell line derived from transfection termed 21, N-O are estimated to produce 10 times more 4.2 kDa β-amyloid protein than CP-7 cells and is chosen for subcloning.

Table 2 illustrates the effect of incubation medium on 4.2 kDa β-amyloid protein levels in selected CHO-K1 cell clones transfected with pCMV-IRES-βAPP$_{695}$.

TABLE 2

| Cell line | Medium | mg protein | RIA, nM | RIA, ng Aβ* per mg protein |
|---|---|---|---|---|
| CP-7 | 1% FCS | 0.53 | 0.85 | 7.0 |
|  | 0.2% BSA | 0.52 | 0.92 | 7.7 |
|  | SFM | 0.52 | 0.51 | 4.2 |
| 21-N-C | 1% FCS | 0.97 | 1.2 | 5.4 |
|  | 0.2% BSA | 0.91 | 2.75 | 13.1 |
|  | SFM | 0.92 | 0.75 | 3.5 |
| 21-N-M | 1% FCS | 0.72 | 1.2 | 7.2 |
|  | 0.2% BSA | 0.71 | 1.3 | 7.9 |
|  | SFM | 0.70 | 1.15 | 7.1 |
| 21-N-O | 1% FCS | 0.70 | 9.2 | 57.1 |
|  | 0.2% BSA | 0.63 | 9.35 | 64.2 |
|  | SFM | 0.72 | 7.9 | 47.4 |
| 22-N-C | 1% FCS | 0.79 | 0.9 | 4.9 |
|  | 0.2% BSA | 0.70 | 1.35 | 8.3 |
|  | SFM | 0.74 | 0.95 | 5.6 |
| 22-N-E | 1% FCS | 0.79 | 0.7 | 3.8 |
|  | 0.2% BSA | 0.77 | 0.65 | 3.6 |
|  | SFM | 0.81 | 0.4 | 2.1 |

*Aβ= 4.2 kDa β-amyloid protein

For the comparison of media, cells are cultured in 6 well plates (9.5 cm$^2$/well) until confluent. Medium is then replaced with 1.5 ml RIA assay medium containing either 1% fetal calf serum (FCS), 0.2% bovine serum albumin (BSA) or no additional material (SFM). After 5 hours medium is collected and 4.2 kDa β-amyloid protein concentrated for RIA determination (as described above). Cell protein is determined after solubilization overnight in 0.5 N NaOH.

Further, the 4.2 kDa β-amyloid protein levels produced by nine subclones of 21-N-O are evaluated by RIA and the data are shown in Table 3.

TABLE 3

| Clone | Protein | RIA, nM | RIA, ng | RIA, ng Aβ per mg protein |
|---|---|---|---|---|
| 21-N-1 | 1.18 | 3.58 | 15.5 | 39.2 |
| 21-N-2 | 1.09 | 5.23 | 22.6 | 62.4 |
| 21-N-3 | 1.27 | 6.39 | 27.7 | 65.4 |
| 21-N-4 | 1.28 | 4.93 | 21.4 | 50.0 |
| 21-N-5 | 1.47 | 6.36 | 27.5 | 56.2 |
| 21-N-6 | 1.48 | 5.23 | 22.6 | 45.9 |
| 21-N-7 | 1.53 | 4.67 | 20.2 | 37.2 |
| 21-N-8 | 1.14 | 6.22 | 26.9 | 71.1 |
| 21-N-9 | 1.3 | 7.32 | 31.7 | 73.2 |

*Aβ=4.2 kDa β-amyloid protein

Level of the 4.2 kDa β-amyloid protein produced by subclones of 21-N-O cells evaluated by RIA is set out in Table 3. The analysis is carried out as follows: Confluent 25 cm$^2$ flasks of cells are incubated with 4 ml RIA assay medium containing 1% FCS for 5 hours as described above. The 4.2 kDa β-amyloid protein are concentrated from 1.5 ml of the medium prior to performing the RIA. Cell protein level is determined after solubilizing the cells in 0.5 N NaOH overnight. Values presented in Table 3 are the means of duplicate determinations.

EXAMPLE 6

Analysis of APP Processing by Pulse-labeling and Immunoprecipitation

The level and pattern of APP processing to 4.2 kDa β-amyloid protein and C-terminal fragments is studied by pulse-labeling and immunoprecipitation of the four selected subclones and results compared to those seen for the parent 21-N-O cell line and CP-7 cells.

Figure 4:
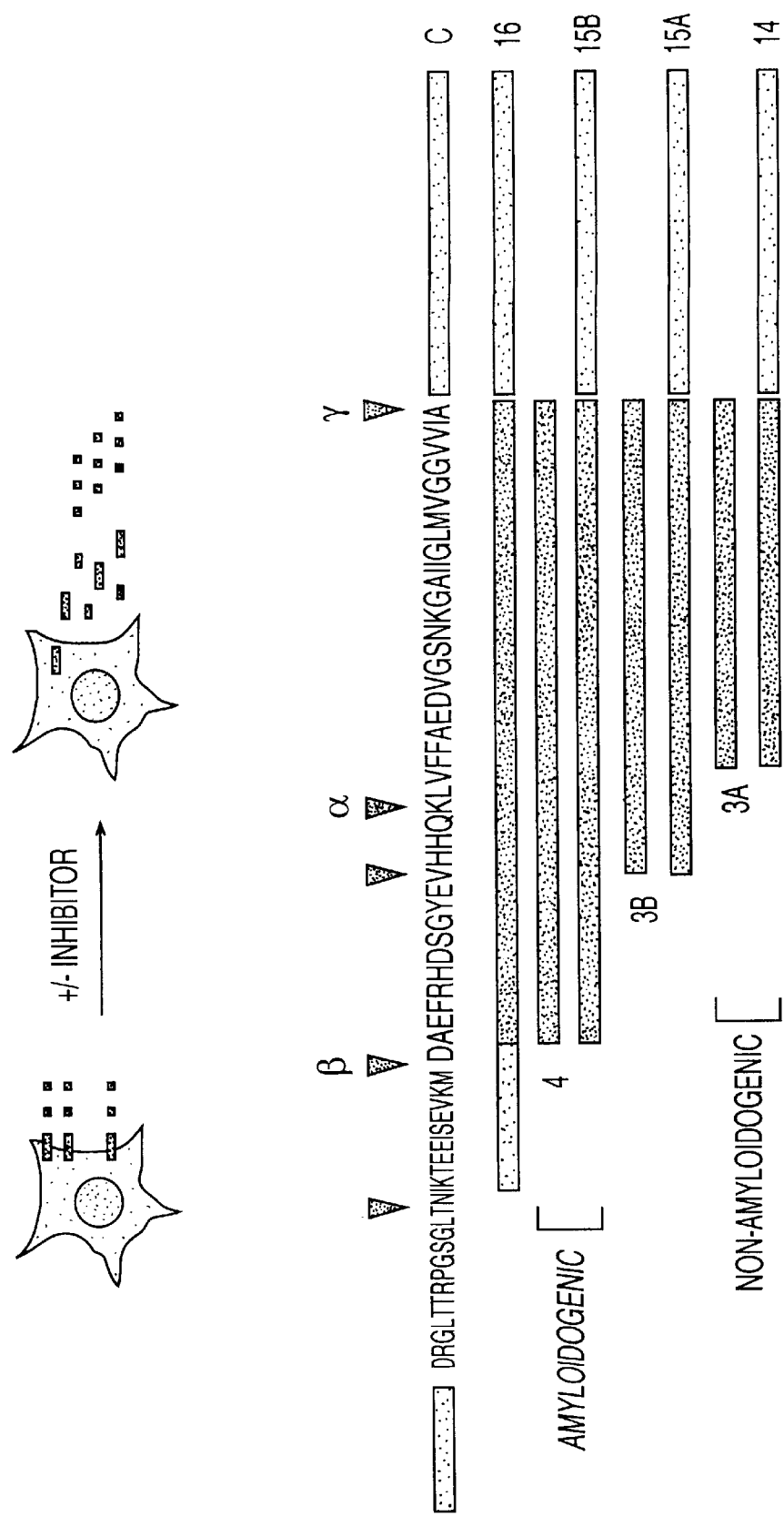
FIG. 4 shows an expected pattern of APP products (SEQ ID NO: 1).

APP production, its processing pattern and the level of 4.2 kDa β-amyloid protein secretion are monitored by pulse-labeling and immunoprecipitation using protocols described by Higaki et al., Neuron 14:651–659 (1995). Essentially, cells are first starved of cysteine and methionine then incubated for 4 hours with medium containing $^{35}$S-methionine and $^{35}$S-cysteine. 4.2 kDa β-amyloid protein secreted into the culture medium is immunoprecipitated using BA#2 rabbit antiserum. Cell associated APP peptides are immunoprecipitated from cell lysates using BA#2 rabbit antiserum which recognizes an epitope near the C-terminal of human APP. The pattern of APP products expected is illustrated in FIG. 4. Peptides present in the media include 4 kDa and 3 kDa products. The 4 kDa products include Aβ1-39 peptide, Aβ1-40 peptide, Aβ1-41 peptide, Aβ1-42 peptide. The 3 kDa peptides include 3A, a reported product of α- and γ-secretase and 3B, which includes peptides 12-39, 12-40, 12-42 and 12-43. C-terminal fragments include portions of the include portions of the membrane and intracellular 100 amino acids C-terminal tail of APP. Variation in the composition or pattern of APP products is indicative of inhibitors of (α-, β, γ-secretase The solubilized immunoprecipitates are separated by SDS polyacrylamide gel electrophoresis and radioactive proteins quantified using a phosphorimager. The areas under each peak are normalized to the amount of cell protein and the labeling patterns compared to those obtained from a control cell line, CP-7 (Scios Nova, Mountain View, Calif.).

The level of 4.2 kDa β-amyloid protein and C-terminal fragments produced by selected subclones of 21-N-O cells are evaluated by pulse labeling and immunoprecipitation. These results are summarized in Table 4 and are used to select two subclones, 21-N-3 and 21-N-9 (21-N-9 was deposited with the American Tissue Type Collection, Rockville Md. on Mar. 26, 1997 and assigned ATCC No CRL 12329), for expansion and further characterization of 4.2 kDa β-amyloid protein production.

TABLE 4

| Cell Line | Aβ | C-terminal fragments | | | |
|---|---|---|---|---|---|
| | | Fragment 14 | Fragment 15A | Fragment 15B | Fragment 16 |
| CP-7 | 0.4 | 1.09 | 0.38 | 0.26 | 0.45 |
| 21-N-O | 0.59 | 8.08 | 2.47 | 2.57 | 3.98 |
| 21-N-2 | 2.72 | 13.4 | 2.64 | 2.98 | 4.59 |
| 21-N-3 | 9.27 | 15.47 | 3.24 | 3.11 | 5.22 |
| 21-N-8 | 2.44 | 13.72 | 1.77 | 2.39 | 4.02 |
| 21-N-9 | 2.22 | 14.68 | 2.04 | 2.29 | 3.83 |

* Aβ=4.2 kDa β-amyloid protein

The immunoprecipitable radioactivity corresponding to 4.2 kDa β-amyloid protein and C-terminal fragments set forth in Table 4 is quantified using a phosphorimager and normalized to the amount of cell protein. Units in Table 4 are in area (mm$^2$)/μg protein.

EXAMPLE 7

Enzyme-linked Immunoassays (ELISA) Analysis of Total 4.2 kDa β-amyloid Protein

Total 4.2 kDa β-amyloid protein is measured with a competitive ELISA using biotinylated Aβ1-28 as a tracer and monoclonal antibody designated 1101.1 which binds to an epitope located between amino acids 13 and 22 of the 4.2 kDa β-amyloid protein (See FIG. 5).

The total 4.2 kDa β-amyloid protein is measured as follows: A 96 well microtitre Maxisorb plate (Nunc, Rochester, N.Y.) is coated with 200 μl/well goat anti-mouse 1 gG Fc specific (Sigma, M-3534, St. Louis, Mo.) at 2.4 μg/ml diluted in 0.1 M sodium bicarbonate buffer and incubated for 2 hours at 37° C. The wells are then washed with phosphate buffered saline (PBS) or PBS/0.05% TWEEN poloxyethyleneysoribtan-20 (4×250 μl). After washing the wells, 200 μl PBS, 0.05% TWEEN-20, 1% BSA (PBS/TWEEN/BSA) or 1% bovine serum albumin in PBS is added to each well and incubated for 1 hour at 37° C.

The solution is removed from the plate and to the plates is added 100 μl per well of the monoclonal antibody designated 1101.1 (concentration of 2.5 ng/ml in PBS/TWEEN/BSA). To each well is added either 100 μl/well of cell supernatant (with or without samples) or 100 μl/well of Aβ1-40 peptide or Aβ1-42 peptide (Bachem, King of Prussia, Pa.) diluted in Buffer A to concentrations ranging from 0.4–100 nM (resulting in final concentrations of 0.1–25 nM—standards are prepared from a 1 mg/ml stock solution dissolved in 20% isopropanol and stored at −20° C.). The samples are then diluted in ELISA assay medium (DMEM (Gibco 041-01965M), 1% non-essential amino acids, 2.5 mM L-glutamine, 0.5 mM Pyruvate, 1% Penicillin, 1% Streptomycin, 0.2% Bovine serum albumin (BSA), Sigma A3296, protease free or Calbiochem 126609)) and incubated overnight at 4° C.

To each sample is added 50 gl/well of biotinylated Aβ1-28 tracer (Neosystems) at a concentration of 8–12 ng/ml in PBS/TWEEN/BSA and the sample is incubated for 1 hour at 4° C. The microtitre dish containing the samples is then inverted and drained on paper towels. 200 μl/well horseradish peroxidase-coupled streptavidin (Zymed, South San Francisco, Calif. 43-4323) diluted 1:3,000 in PBS/TWEEN/BSA is added to the drained microtitre dish. The samples are then incubated for 1 hour at 4° C. After the samples are incubated, the wells are washed with PBS+0.05% TWEEN-20 (PBS/TWEEN) (5×200 μl). Following the washing, 200 μl/well of tetramethylbenzidine (TMB) (Sigma T-5525) is added to the wells. The microtitre dishes are then incubated for between 15 minutes and 1 hour at room temperature. Incubation of the samples is terminated by stopping the reaction with 100 μl/well 2.5 M $H_2SO_4$. The absorbance $_{450}$ of the samples is measured.

EXAMPLE 8

Enzyme-linked Immunoassays (ELISA) Analysis of Aβ1-40 Peptide and Aβ1-42 Peptide Aβ1-40 peptide and Aβ1-42 peptide are measured by sandwich ELISAs using mAb 1101.1 as a capture antibody and either rabbit antiserum BA#1 or mAb 1702.1 which binds to the C-terminus of Aβ1-40 peptide or mAb 108.1 which binds to the C-terminus of Aβ1-42 peptide. The epitopes of Aβ peptides recognized by the antibodies used for the RIA and ELISAs are shown in FIG. 5.

1. Sandwich ELISA for Aβ1-40 Peptide

To each well is added either 100 μl/well of cell supernatant to be analyzed or 100 μl Aβ1-40 peptide or Aβ1-42 peptide (Bachem, King of Prussia, Pa.) at concentrations ranging from 0.0137 ng/well to 10 ng/well. The standards are prepared in the ELISA assay meduim (DMEM (Gibco 041-01965M), 1% non-essential amino acids, 2.5 mM L-glutamine, 0.5 mM pyruvate, 1% penicillin, 1% streptomycin, 0.2% bovine serum albumin (Sigma A3296 protease free or Calbiochem 126609)) which is the same as the cell culture meduim. The wells are incubated overnight at 4° C. After the overnight incubation the plates are washed with PBS/TWEEN (3×250 μl per well) and 100 μl/well of BA#1 rabbit antiserum diluted 1:2,000 or 1:4,000 in PBS/TWEEN+0.1% BSA is added to each well. The microtitre plates are then incubated for 2 hours at 37° C. After incubation, the wells are washed with PBS/TWEEN (3×250 μl ) and 100 μl/well of horseradish peroxidase-conjugated donkey or goat anti-rabbit 1 gG, pre-adsorbed with mouse serum proteins, diluted 1:3,000 or 1:5,000 in PBS/TWEEN/BSA is added. The microtitre plates are then incubated for 2 hours at 37° C. and washed with PBS/TWEEN (3×250 μl per well). To the wells is added 100 ul/well of freshly prepared or pre-made TMB substrate (Sigma T-5525, St. Louis, Mo.)(prepared by dissolving one 1 mg tablet in 1 ml DMSO and then adding 9 ml of phosphate-citrate buffer (0.2 M dibasic sodium phosphate, 0.1 M citric acid, pH 5.0); add 2 μl of fresh 30% $H_2O_2$ for 10 ml of substrate solution immediately prior to use. After approximately 7 minutes (as needed for color to develop), 100 μl/well of 2.5 M $H_2SO_4$ is added to stop the reaction and absorbance at 450 nm is read.

2. Sandwich ELISA for Aβ1-42 Peptide 96 well microtitre plates are incubated overnight at 4° C. containing 100 μl/well of a 4 μg/ml solution of purified mAb 110.1.1 diluted in PBS. After this incubation, the microtitre plates are washed with PBS/TWEEN (3×250 μl per well) and the wells are blocked with 125 μl/well of 0.5% BSA in PBS for 1 hour at 37° C.

The blocked wells are then washed with PBS/TWEEN (3×250 μper well) and 100 μl/well of medium or peptide standards (Aβ-42 peptide, Bachem, King of Prussia, Pa.) diluted in assay medium is added to each well. The plates are covered then incubated overnight at 4° C. After the overnight incubation, the microtitre plates are washed with PBS/TWEEN (3×250 μl per well) and 100 μl/well of biotinylated mAb 108.1 diluted from 0.5 mg/ml aliquots to 0.75 μg/ml in PBS/TWEEN +0.1% BSA is added to each well. The plates are then incubated for 2 hours at 37° C. or 4 hours at room temperature. After this incubation, the microtitre dishes are washed with PBS/TWEEN (3×250 μl per well) and 100 μl/well of horseradish peroxidase-conjugated streptavidin diluted 1:10,000 or 1:20,000 in PBS/TWEEN/BSA is added.

The samples are then incubated for 15 or 30 minutes at room temperature prior to being washed with PBS/TWEEN (3×250 μl per well). To the washed wells is added 100 μl/well of freshly prepared TMB substrate prepared by dissolving one 1 mg tablet in 1 ml DMSO to which is added 9 ml of phosphate-citrate buffer (0.2 M dibasic sodium phosphate, 0.1 M citric acid, pH 5.0) and 2 μl of fresh 30% $H_2O_2$ for 10 ml of substrate solution immediately prior to use. After approximately 7 minutes (as needed for color to develop) 100 μl/well of 2.5 M $H_2SO_4$ is added to stop the reaction and absorbance at 450 nm is read.

Figure 6A:
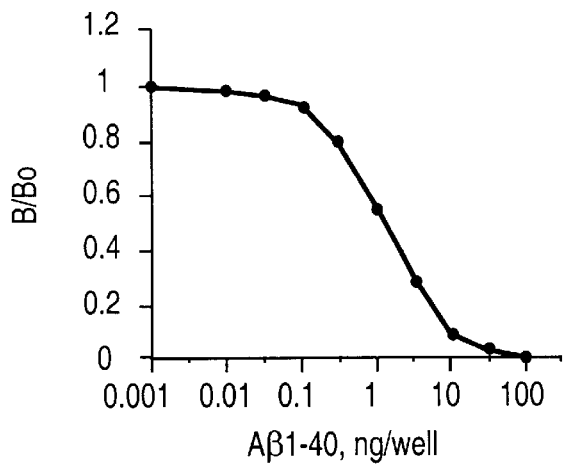
FIGS. 6A–6C depict standard curves of the competition ELISA for total 4.2 kDa β-amyloid protein, the sandwich ELISA for Aβ1-40 peptide and the sandwich ELISA for Aβ1-42 peptide.
Figure 6B:
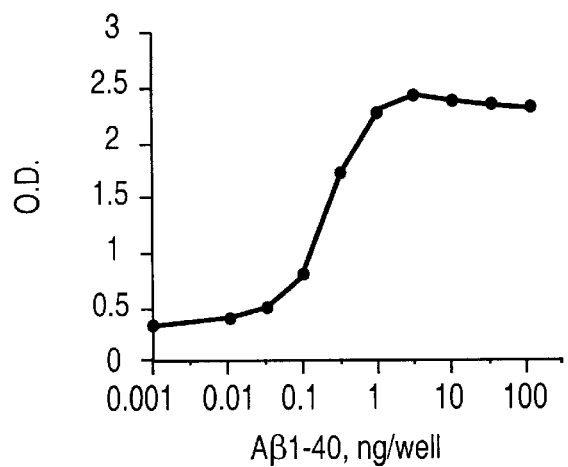
Figure 6C:
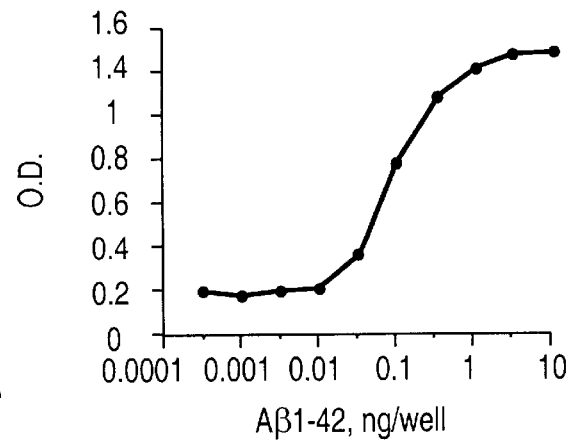
Figure 7:
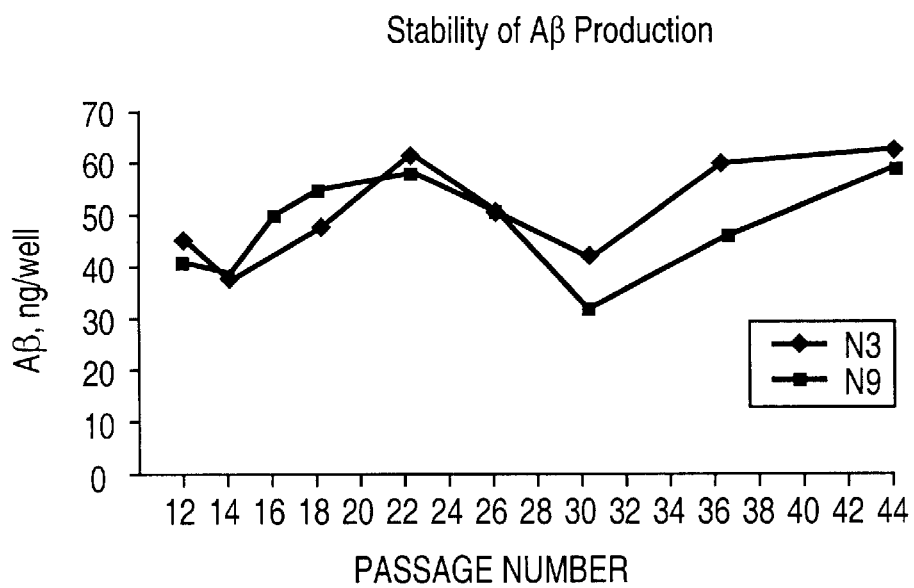
FIG. 7 illustrates the stability of 4.2 kDa β-amyloid protein in cell lines 21-N-3 (N3) and 21-N-9 (N9).
Figure 8:
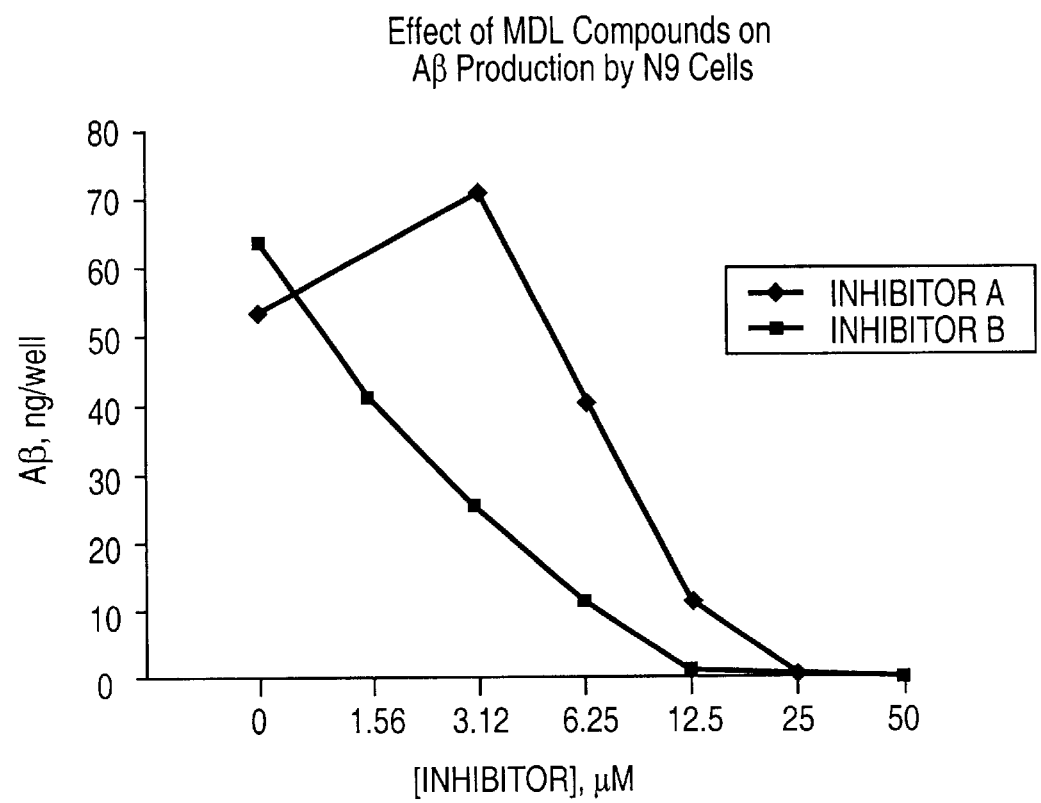
FIG. 8 illustrates the effect of inhibitor compounds on 4.2 kDa β-amyloid protein production by 21-N-9 cells.

The various forms of 4.2 kDa β-amyloid protein produced by 21-N-3 and 21-N-9 cells are quantified using selective ELISAs for total 4.2 kDa β-amyloid protein, Aβ1I-40 peptide and Aβ1-42 peptide. Typical standard curves for these three assays are shown in FIG. 6. 4.2 kDa β-amyloid protein are collected in an assay medium using DMEM and 0.2% BSA and assayed directly without a concentration step. The level of the peptides measured in the different cell lines is shown in Table 5. Both 21-N-3 and 21-N-9 secreted 10–15 times more 4.2 kDa β-amyloid protein than CP-7 cells. The secretion rate for these cell lines is estimated at about 5 ng of 4.2 kDa β-amyloid protein (total) per 100 μl medium during 4 hours when cells are cultured at density of 0.5–1× $10^5$ cells per well in 96 well plates (surface area ~0.4 $cm^2$). The two cell lines are analyzed for their stability by measuring the amount of 4.2 kDa β-amyloid protein secreted with time in culture (FIG. 7) following re-establishment of these cell lines from frozen stocks. The use of these cell lines for identifying inhibitors of 4.2 kDa β-amyloid protein production is validated using compounds previously identified using the CP-6 cell line (FIG. 8).

Table 5 sets forth estimates of the different forms of 4.2 kDa β-amyloid protein secreted from cell lines.

TABLE 5

| Cell line | Total *Aβ, ng | Aβ1-40, ng | Aβ1-42, ng |
|---|---|---|---|
| CP-7 | 0.68 | 0.18 | 0.02 |
| 21-N-3 | 8.83 | 0.66 | 0.14 |
| 21-N-9 | 7.9 | 0.68 | 0.12 |

*Aβ= 4.2 kDa β-amyloid protein

To obtain the data in Table 5, cells are cultured in 6 well dishes at a density of 5×$10^5$ cells/well. The following day culture medium is replaced with 2 ml DMEM assay medium containing 0.2% BSA. After 4 hours medium is collected and stored at −20° C. until assayed for 4.2 kDa β-amyloid protein using the three ELISAs described above. FIG. 5 diagramatically illustrates the epitopes of 4.2 kDa β-amyloid protein recognized by the antibodies, 1101.1, BA#1 and 108.1. By substituting mAb 1702.1 (1.75 μg/ml) for mAb 108.1 in the foregoing protocal, a sandwich ELISA fs carried out for Aβ1-40 peptide.

EXAMPLE 9

The Effect of Inhibitors on 4.2 kDa β-amyloid Protein Formation

Putative inhibitors are dissolved in DMSO and diluted in RIA assay medium containing 0.2% BSA. 21-N-9 cells are incubated for 5 hours in the presence of putative inhibitors. After five hours, medium is collected and the 4.2 kDa β-amyloid protein levels are determined by RIA without prior concentration as described above. The results are set forth in FIG. 8. The data presented is the mean of duplicate determinations.

EXAMPLE 10

High Throughput Assay

21-N-9 cells (200 μl of a stock at an approximate concentration of $4\times10^5$ cells/ml) are seeded in a 96 well microtitre plate (Costar) in culture medium (DMEM/NUT MIX F-12 (Gibco,/BRL, Gaithersburg, Md.). The microtitre plates are incubated overnight at 37° C. in 5% $CO_2$. The cells are then washed with PBS (1×200 μ). To the wells is added 10 μl of the 20× inhibitor solution (dissolved in DMSO) and 190 μl assay medium (MEM (Gibco/BRL, Gaithersburg, Md.), 1% non-essential amino acids, 2.5 mM L-glutamine, 0.5 mM Pyruvate, 1% penicillin, 1% streptomycin and 0.2 bovine serum albumin (BSA, Calbiochem, La Lolla, Calif.). The microtitre plate is then incubated at 37° C., 5% $CO_2$ for 4 hours. The level of 4.2 kDa β-amyloid protein is estimated using the procedure set forth in Example 7.

---

We claim:

1. An eukaryotic cell line having a exogenous gene construction, said exogenous gene construction comprising a cytomegalovirus promoter encoding sequence, a strong ribosome binding site encoding sequence, a β-amyloid precursor protein encoding sequence, a selectable marker encoding sequence, and a poly-adenylation signal encoding sequence.

2. The eukaryotic cell line according to claim 1, wherein said exogenous gene construction is capable of stably expressing a β-amyloid precursor protein molecule.

3. The eukaryotic cell line according to claim 1, wherein said exogenous gene construction further comprises an internal ribosome entry site encoding sequence.

4. The eukaryotic cell line according to claim 1, wherein said β-amyloid precursor protein encoding sequence encodes the 695 amino acid isoform of human β-amyloid precursor protein molecule.

5. The eukaryotic cell line according to claim 1, wherein said β-amyloid precursor protein encoding sequence encodes the 751 amino acid isoform of human β-amyloid precursor protein molecule.

6. The eukaryotic cell line according to claim 1, wherein said eukaryotic cell line is selected from the group consisting of chinese hamster ovary cell line, dihydrofolate reductase deficient hamster cell line, human kidney cell line, rat neuroglimo cell line, human neuroglimo cell line, and rat neuroblastoma cell line.

7. The eukaryotic cell line according to claim 6, wherein said eukaryotic cell line is chinese hamster ovary cell line.

8. The eukaryotic cell line according to claim 7, wherein said eukaryotic cell line is chinese hamster ovary cell line K1.

9. The eukaryotic cell line according to claim 1, wherein the selectable marker encoding sequence is selected from the group consisting of: neomycin phosphotransferase encoding sequence, dihydrofolate reductase encoding sequence, xanthine-guanine phosphoribosyltransferase encoding sequence, aspartate transcarbamoylase encoding sequence, adenosine deaminase encoding sequence, adenylate deaminase encoding sequence, UMP synthetase encoding sequence, glutamine synthetase encoding sequence, asparagine synthetase encoding sequence ornithine decarboxylase encoding sequence, the thymidine kinase encoding sequence; the aminoglycosidase phosphotransferase encoding sequence; hygromycin B phosphotransferase encoding sequence; and the CAD encoding sequence.

10. The eukaryotic cell line according to claim 9, wherein the selectable marker encoding sequence is bacterial neomycin phosphotransferase encoding sequence.

11. The eukaryotic cell line according to claim 3, wherein said internal ribosome site encoding sequence is an encephalomycocarditis virus internal ribosome entry site encoding sequence linked to said β-amyloid precursor protein encoding sequence.

12. The eukaryotic cell line according to claim 11, wherein said β-amyloid precursor protein encoding sequence encodes the 695 amino acid isoform of human β-amyloid precursor protein molecule.

13. The eukaryotic cell line according to claim 11, wherein said β-amyloid precursor protein encoding sequence encodes the 751 amino acid isoform of human β-amyloid precursor protein molecule.

14. The eukaryotic cell line according to claim 11, wherein the selectable marker encoding sequence is selected from the group consisting of: neomycin phosphotransferase encoding sequence, dihydrofolate reductase encoding sequence, xanthine-guanine phosphoribosyltransferase encoding sequence, aspartate transcarbamoylase encoding sequence, adenosine deaminase encoding sequence, adenylate deaminase encoding sequence, UMP synthetase encoding sequence, glutamine synthetase encoding sequence, asparagine synthetase encoding sequence ornithine decarboxylase encoding sequence, the thymidine kinase encoding sequence; the aminoglycosidase phosphotransferase encoding sequence; hygromycin B phosphotransferase encoding sequence; and the CAD encoding sequence.

15. The eukaryotic cell line according to claim 14, wherein the selectable marker encoding sequence is bacterial neomycin phosphotransferase encoding sequence.

16. The eukaryotic cell line according to claim 1, wherein said strong ribosome binding site encoding sequence is linked to said β-amyloid precursor protein encoding sequence and said cytomegalovirus promoter encoding sequence to provide efficient expression of said β-amyloid precursor protein encoding sequence.

17. The eukaryotic cell line according to claim 16, wherein said β-amyloid precursor protein encoding sequence encodes the 695 amino acid isoform of human β-amyloid precursor protein molecule.

18. The eukaryotic cell line according to claim 16, wherein said β-amyloid precursor protein encoding sequence encodes the 751 amino acid isoform of human β-amyloid precursor protein molecule.

19. A eukaryotic cell line selected from the group consisting of 21-N-1, 21-N-2, 21-N-3, 21-N-4, 21-N-5, 21-N-6, 21-N-7, 21-N-8, and 21-N-9.

20. The eukaryotic cell line according to claim 19, wherein said eukaryotic cell line is selected from the group consisting of 21-N-9 and 21-N-3.

21. The eukaryotic cell line according to claim 20, wherein said eukaryotic cell line is 21-N-9.

22. An eukaryotic cell line having a exogenous gene construction, said exogenous gene construction comprising a cytomegalovirus promoter encoding sequence, a ribosome binding site encoding sequence, a β-amyloid precursor protein encoding sequence, a selectable marker encoding sequence, and a poly-adenylation signal encoding sequence.

23. A substantially purified nucleic acid molecule that encodes, in order:

a cytomegalovirus promoter;

a ribosome binding site;

a β-amyloid precursor protein molecule;

a selectable marker; and a poly-adenylation signal.

24. A substantially purified nucleic acid molecule that encodes, in order:

a cytomegalovirus promoter;

a strong ribosome binding site;

a β-amyloid precursor protein molecule;

a selectable marker; and a poly-adenylation signal.

25. A nucleic acid molecule comprising pCMV-IRES-βAPP$_{695}$.

26. A composition comprising a eukaryotic cell line and an inhibitor of a β-amyloid processing pathway, said eukaryotic cell line having a exogenous gene construction, said exogenous gene construction comprising a cytomegalovirus promoter encoding sequence, a strong ribosome binding site encoding sequence, a β-amyloid precursor protein encoding sequence, a selectable marker encoding sequence, and a poly-adenylation signal encoding sequence.

* * * * *